(12) United States Patent
Bates et al.

(10) Patent No.: US 6,670,574 B1
(45) Date of Patent: Dec. 30, 2003

(54) LASER WELD MONITOR

(75) Inventors: Gregory Bates, Stevenson Ranch, CA (US); Girish Kelkar, Cerritos, CA (US)

(73) Assignees: Unitek Miyachi Corporation, Monrovia, CA (US); Miyachi Technos Corporation, Noda (JP)

( * ) Notice: Subject to any disclaimer, the term of this patent is extended or adjusted under 35 U.S.C. 154(b) by 0 days.

(21) Appl. No.: 10/210,009

(22) Filed: Jul. 31, 2002

(51) Int. Cl.[7] ............................................... B23K 26/00
(52) U.S. Cl. ........................... 219/121.64; 219/121.85; 219/121.83; 219/121.63
(58) Field of Search ................ 219/121.64, 121.85, 219/121.83, 121.63, 121.65, 121.66, 121.78

(56) References Cited

U.S. PATENT DOCUMENTS

| | | |
|---|---|---|
| 4,007,631 A | 2/1977 | Saifi et al. |
| 4,419,562 A | 12/1983 | Jon et al. |
| 4,446,354 A | 5/1984 | Kearney |
| 4,649,256 A | 3/1987 | Minamida et al. |
| 5,001,324 A | 3/1991 | Aiello et al. |
| 5,038,016 A | 8/1991 | Robertson et al. |
| 5,045,669 A | 9/1991 | Ortiz, Jr. et al. |
| 5,155,329 A | 10/1992 | Terada et al. |
| 5,247,155 A * | 9/1993 | Steen et al. ............ 219/121.83 |
| 5,272,312 A | 12/1993 | Jurca |
| 5,286,947 A | 2/1994 | Clyde et al. |
| 5,314,248 A | 5/1994 | Manassero et al. |
| 5,360,960 A | 11/1994 | Shirk |
| 5,506,386 A | 4/1996 | Gross |
| 5,607,605 A | 3/1997 | Musasa et al. |
| 5,651,903 A | 7/1997 | Shirk |
| 5,674,415 A | 10/1997 | Leong et al. |
| 5,681,490 A | 10/1997 | Chang |
| 5,728,992 A | 3/1998 | Swidwa |
| 5,886,319 A | 3/1999 | Preston et al. |
| 6,075,220 A | 6/2000 | Essien et al. |
| 6,188,041 B1 | 2/2001 | Kim et al. |
| 6,204,469 B1 | 3/2001 | Fields, Jr. et al. |
| 6,329,635 B1 | 12/2001 | Leong et al. |
| 6,344,625 B1 | 2/2002 | Kim et al. |

FOREIGN PATENT DOCUMENTS

| | | |
|---|---|---|
| DE | 004106008 A1 | 8/1992 |
| DE | 004234339 A1 | 4/1994 |
| JP | 405337664 A | 12/1993 |
| JP | 408164489 A | 3/1999 |
| JP | 411077345 A | 3/1999 |
| JP | 02000084683 A | 3/2000 |
| JP | 02000271768 A | 10/2000 |

* cited by examiner

Primary Examiner—M. Alexandra Elve
(74) Attorney, Agent, or Firm—Christie, Parker & Hale, LLP

(57) ABSTRACT

A laser weld monitoring system capable of assessing a weld quality of welding using a pulsed laser is provided. The system includes at least one sensor capable of capturing a weld characteristic of welding using said pulsed laser. The weld characteristic has multiple attributes. The system also includes data acquisition and processing equipment adapted for storing and analyzing the weld characteristic. A user first performs multiple welds to capture at least one weld characteristic for each weld. The user then determines the weld quality of each weld, and runs at least one of a library of algorithms associated with the attributes on said at least one weld characteristic for each weld to generate a single value output for the associated attribute. The user selects an attribute indicative of the weld quality by correlating the single value outputs of said at least one algorithm with the weld qualities of the welds.

22 Claims, 18 Drawing Sheets

LASER WELD MONITOR

FIELD OF THE INVENTION

The present invention is related to laser welding, and particularly to a method and apparatus for monitoring weld quality during pulsed laser welding. The present invention can be used for both process development and process control of welding.

BACKGROUND

Lasers are often used for welding as a non-contact energy source that requires minimum heat input. In particular, low power pulsed Nd:YAG lasers exhibiting high peak powers combined with small spot sizes can heat materials above their melting point, without significantly raising temperature next to the weld pool. Advanced features such as pulse shaping and laser power feedback have further improved solid-state lasers by providing increased control of the laser output. However, even with these advanced features, prediction of laser-material interaction is not straight forward; therefore, it is difficult to develop a reliable and easy-to-use laser weld monitoring system.

Conventional monitoring techniques use sensors such as infrared (IR), ultraviolet (UV), high-speed camera, sound, and transducer acoustic. However, it is often difficult to analyze the monitored weld characteristics to distinguish between good and bad welds because of the non-trivial nature of predicting laser-material interaction. Further, complex pattern matching and/or advanced mathematical techniques are often employed to analyze the profiles taken, further complicating the analysis and application process. Because of the complicated nature of the conventional monitoring techniques and difficulties associated with the analysis, users often do not understand the monitoring process, and instead rely entirely on the system developers to produce a system that will meet their process development and/or process control needs.

Therefore, it is desirable to provide a method and apparatus for capturing the weld characteristics, for analyzing the captured weld characteristics using simple mathematical algorithms, and for applying the analysis to distinguish between good and bad welds that are easier to understand and customizable to meet the process development and process control needs of each individual user.

SUMMARY

In an exemplary embodiment according to the present invention, a laser weld monitoring system capable of assessing weld quality of welds using a pulsed laser is provided. The system includes at least one sensor capable of capturing a weld characteristic of welding using said pulsed laser, said weld characteristic having a plurality of attributes; and data acquisition and processing equipment adapted for storing and analyzing said weld characteristic, wherein a user performs a plurality of welds to capture at least one weld characteristic for each weld, determines the weld quality of each weld, runs at least one of a library of algorithms associated with the attributes on said at least one weld characteristic for each weld to generate a single value output for the associated attribute, and selects an attribute indicative of the weld quality by correlating the single value outputs of said at least one algorithm with the weld qualities of the welds.

In another exemplary embodiment according to the present invention, a method of monitoring a weld quality of a pulsed laser is provided. The method comprises: performing a plurality of test welds; capturing at least one weld characteristic of each test weld, said at least one weld characteristic having a plurality of attributes; determining the weld quality of each test weld; running at least one of a library of algorithms associated with the attributes on said at least one weld characteristic for each weld to generate a single value output for the associated attribute; and selecting an attribute indicative of the weld quality by correlating the single value outputs of said at least one algorithm with the weld qualities of the test welds.

In yet another exemplary embodiment according to the present invention, a method of adjusting a focus height of a pulsed laser is provided. The method includes: performing a plurality of test welds, each test weld being performed at a different focus height about a predetermined initial focus height; capturing a temperature characteristic of each test weld; and determining the focus height that results in a maximum rising slope in the temperature characteristic as a correct focus height.

BRIEF DESCRIPTION OF THE DRAWINGS

These and other aspects of the invention may be understood by reference to the following detailed description, taken in conjunction with the accompanying drawings, wherein.

DETAILED DESCRIPTION

Figure 1:
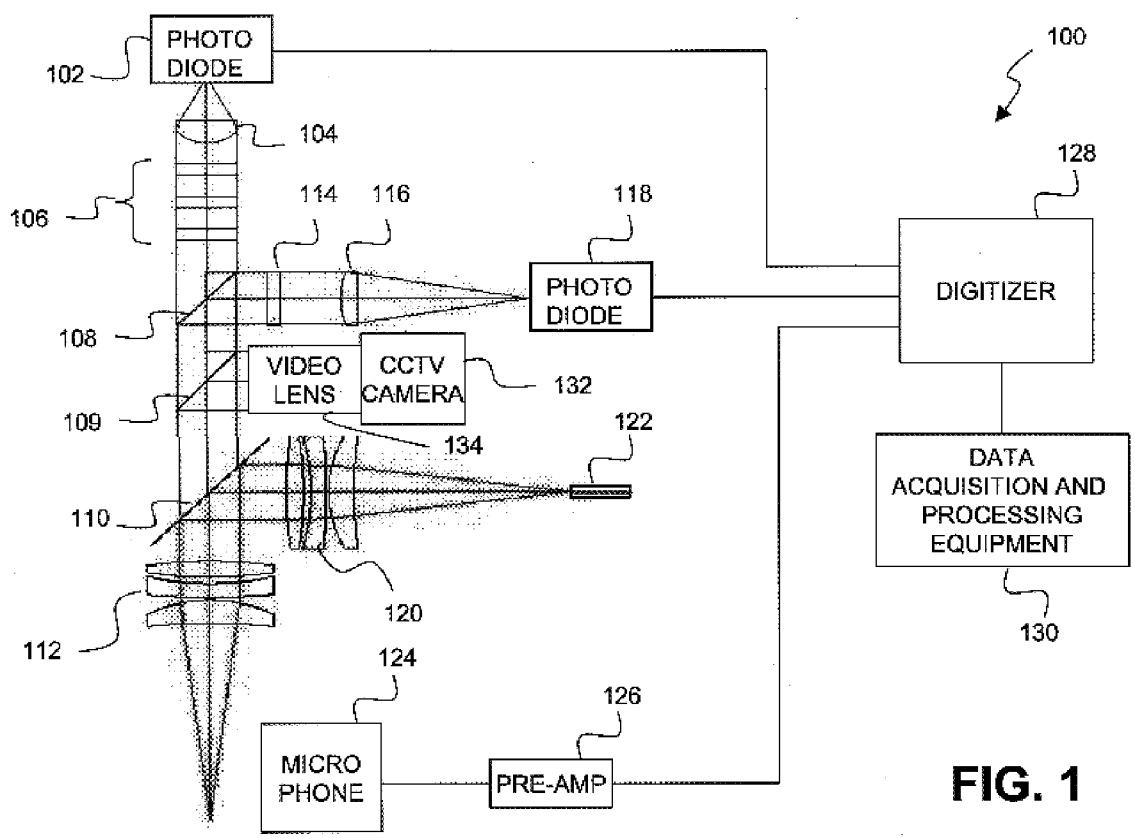
FIG. 1 is a block diagram of a laser weld monitoring system for capturing weld characteristics in an exemplary embodiment according to the present invention.

FIG. 1 is a block diagram of a weld monitoring system 100 for capturing (or measuring) and analyzing laser weld characteristics in an exemplary embodiment according to the present invention. The weld monitoring system 100 may be used for either or both process development and process control. In this exemplary embodiment, three signals, namely, reflected laser radiation, infrared radiation and acoustic air, are captured by a corresponding number of sensors.

Further, a closed circuit television (CCTV) camera is used to capture images of welding parts prior to and/or after welding. Analysis (e.g., with the help of frame grabber type software) of the images prior to welding may allow verification of part identification and positioning. For example, the captured images may be used to align the laser beam to the weld location. Post-weld images may allow confirmation of weld location and spot size. Such information gathered from the images, either qualitative or quantitative, may be used in conjunction with single value outputs of the algorithms and/or test data to define weld quality.

The reflected laser radiation ("reflection" or "reflected signal") may be used as an indicator of weld quality because metals have a high initial reflectivity, which, however, decreases rapidly at melting temperature. Further, melt pool shape changes reflection signal due to directionality. For example, a concave shape of welding surface may lead to increased absorption, and decrease in signal. In addition, a flat shape may lead to direct reflection back, resulting in a strong signal. Further, a convex shape may lead to reflection away from the sensor, thus resulting in decreased signal strength.

The infrared (IR) radiation due to the weld pool heat ("temperature signal," "IR signal" or "infrared signal") depends on the surface temperature. The IR signal is indicative of weld pool temperature, but not a measure of the exact temperature of the weld pool. The IR signal may indicate the level and rate of heating and the ability of material to conduct heat away from the surface. Further, IR signal depends on weld surface area size and melt pool flow. As a nugget grows, more surface area is available to emit IR radiation. The IR signal also depends on emissivity of the base material where low emissivity materials have high reflection. Emissivity values may change with temperature.

The acoustic air ("acoustic", "acoustic signal" or "airborne acoustic waves") is caused by an interaction of the melt pool (typically very hot) with the ambient air (typically relatively cool). Tones are created by pressure changes. The ideal gas law of PV=nRT may come into play here, where P=pressure, V=volume, n=number of moles, R=constant (e.g., 0.0821) and T=temperature Kelvin. When differentiated, (dP/dt)V=nR (dT/dt). Thus, if the temperature change with respect to time is small, then the pressure change and therefore the acoustic signal is small. If, however, the temperature change with respect to time is large, then the pressure change and therefore the acoustic signal is large.

A photodiode 118 is used to measure the reflection signal (e.g., 1064 nm (nano-meter)) from the surface. The photodiode 118, for example, may be a Si (silicon) photodiode with a peak response at 800 nm. In addition, a photodiode 102 is used to measure the IR signal. The photodiode 102, for example, may be an InGaAs (indium gallium arsenide) photodiode with a peak response at 1550 nm. Further, a microphone 124 is used to measure the acoustic signal. The microphone 124, for example, may be a 20-20 kHz flat response microphone. In other embodiments, other sensors or detectors (e.g., monitor sensor, plasma sensor, machine vision sensor, etc.) instead of or in addition to the photodiodes 102, 118 and/or the microphone 124 may be used to measure laser weld characteristics.

In the laser weld monitoring system 100 of FIG. 1, clean, low-noise signals from the photodiodes 102, 118 and the microphone 124 are provided to a digitizer 128 (which may be an oscilloscope, such as a digital oscilloscope) for an analysis of different laser weld characteristics. A data acquisition and processing equipment 130 (e.g., a computer or an automatic data processing equipment, and may be referred to as a data processing equipment) is coupled to the digitizer 128 to process (e.g., perform analog-to-digital conversion) the measured weld characteristics.

The data acquisition and processing equipment 130 may include a system-on-chip (SOC). In other embodiments, the digitizer 128 and the data acquisition and processing equipment 130 may be integrated as a single monitoring device, and may together be referred to as a data acquisition and processing equipment. For example, the digitizer 128 may be a DSP (digital signal processing) and/or DAQ (data acquisition) board implemented in a data acquisition and processing equipment in other embodiments. In still other embodiments, the analysis of the measured weld characteristics may be performed manually with little or no use of a data acquisition and processing equipment.

A laser signal may be provided via a fiber optic cable 122, which for example, may be any multi-mode optical fiber, such as, for example, a 600SI (600 μm diameter, step index) optical fiber. The laser is not necessarily a part of the weld monitoring system 100, and any suitable pulsed laser may be used. For example, the laser signal may be provided by a pulsed Nd:YAG laser, which for example, may generate laser beam (e.g., with power of less than 500W (Watts)) at 1064 nm. In other embodiments, any other suitable laser, such as, for example, a feedback laser, a non-feedback laser, a $CO_2$ laser or a green laser may be used instead. At the output of the fiber optic cable 122, the laser signal passes through a collimator 120, which may be any suitable collimator, such as, for example, a 100H COL (100 mm high density collimator) available from Unitek-Miyachi Corporation, Monrovia, Calif.

The laser signal then may be applied to a dichroic mirror 110, which for example, may reflect 99.5% at 1064 nm and 10% at 633 nm. This way, most of the 1064 nm laser beam is reflected and applied to the welding surface. The reflected laser signal is focused by a focus lens 112, which may be any suitable focus lens, such as, for example, a 100H FOC (100 high density focus lens).

Some portion of the laser signal is reflected back from the welding surface. An optical signal (e.g., including the reflected signal) passes through the focus lens 112 and the dichroic mirror 110, and is applied to a cold mirror 109. The cold mirror 109, for example, may reflect 90% at 450–750 nm and may reflect only 10% in IR (infrared). A portion of the optical signal reflected by the cold mirror 109 is provided to a CCTV camera 132 through a video lens 134. In the described embodiment, the CCTV camera 132 is co-axial with the weld process, in which the camera is in-line with the weld nugget image and/or weld location. Further, working or image distance of the CCTV camera 134 is not lengthened appreciably. However, the cold mirror 109 may reflect and/or absorb some of the IR radiation, and the IR radiation travels a larger distance, thus may lead to a reduced signal.

The output of the CCTV camera 134 may also be provided to the digitizer 128 for analysis. The digitizer may be customized for image capture and may include a frame grabber. The reflected signal that passes through the cold mirror 109 reflects off the dichroic mirror 108 (e.g., 100% at 1064 nm and 10% at 663 nm), gets filtered at 1064 nm with an interference filter 114 (e.g., 1064+/−10 nm interference filter), and is focused onto the photodiode 118 by a lens 116, which for example, may be a 75 mm (mili-meter) plano-convex lens.

The photodiode 118, for example, may have a good sensitivity at 1064 nm and may respond quickly. The output of the photodiode 118 is applied to the digitizer 128 for waveform viewing and/or analysis. In other embodiments, the digitizer 128 may not be used, and instead, the photodiode output may be provided directly to the data acquisition and processing equipment 130, which may have the functionality of a digitizer. In still other embodiments, a low pass filter, such as, for example, a 3-pole 15 kHz (kilo-Hertz) low pass filter may be used to remove the electrical noise attributed to a weld laser and a stepper motor (e.g., used for moving the focus lens 112 to move the weld laser in and out of focus).

An IR signal from the weld surface passes through the focus lens 112, the dichroic mirrors and the cold mirror 109, and gets filtered by three long pass filters 106 (e.g., at >1400 nm), and is focused on to a photodiode 102 by a lens 104, which for example, may be a 25 mm plano-convex lens. Three long pass filters are used in this case but the number may decrease or increase depending on the application. According to the Stefan-Boltzmann law, the melting points of most metals show good response in the 1400–1700 nm range. Therefore, the photodiode 102, for example, may have a strong sensitivity in the 1400–1700 nm range. The 25 mm plano-convex lens may improve signal strength by a factor of 10, for example. The long pass filters 106 (e.g., each with an OD 3 (optical density for transmittance of $10^{-3}$) in the stop band) may be used to reduce or eliminate the 1064 nm signal leaking through. In other embodiments, more or less than three long pass filters may be used.

The output of the photodiode 102 is also provided to the digitizer 128 for processing and analysis. When the digitizer 128 is an oscilloscope, it may also be used for waveform viewing. In other embodiments, a 3-pole 15 kHz low pass filter may be placed between the photodiode 102 and the digitizer 128, similar to the case of the output from the photodiode 118.

The microphone 124 is used to sense the acoustic signal caused by rapid expansion of air adjacent to the weld. A pre-amplifier 126 raises the signal to suitable values prior to being provided to the digitizer 128. In other embodiments, the microphone 124 and the pre-amplifier 126 may be a single integrated device. In other embodiments, a low pass filter, such as, for example, a 3 pole 15 kHz low pass filter may be used between the pre-amplifier 126 and the digitizer 128. The low pass filter, for example, may reduce or eliminate a 20 kHz signal which may be present due to the laser power supply IGBT (insulated gate bipolar transistor). The 20 kHz signal may be absent for non-feedback lasers, such as, for example, LW 52 (a Unitek-Miyachi laser welder) or any other non-power feedback laser welder.

The weld surface, for example, may be formed from stainless steel (e.g., 304SS) since Nd:YAG radiation couples well with 304SS and the material is very weldable. Use of 304SS may allow the results to be interpreted purely from geometry issues without distortion from material effects. In other embodiments, the weld surface may be copper, aluminum or any other suitable metal or alloy known to those skilled in the art.

The output of the photodiodes 102, 118 and the microphone 124 may be initially displayed on the digitizer 128 (when it is an oscilloscope) during and/or after the weld. The digitizer 128 may include one or more of a data acquisition board (DAQ), a digital signal processing (DSP) board and/or custom electronics. In other embodiments, the indication of sensor outputs may be provided by any suitable device, such as, for example, LED (light emitting diode) illumination.

In an exemplary embodiment according to the present invention, algorithms have been developed to analyze the raw monitor signals for the purpose of interpretation and decision-making. The algorithms may be formulated with relatively simple mathematical techniques such as integration and maximum value as illustrated in FIG. 2.

Figure 2:
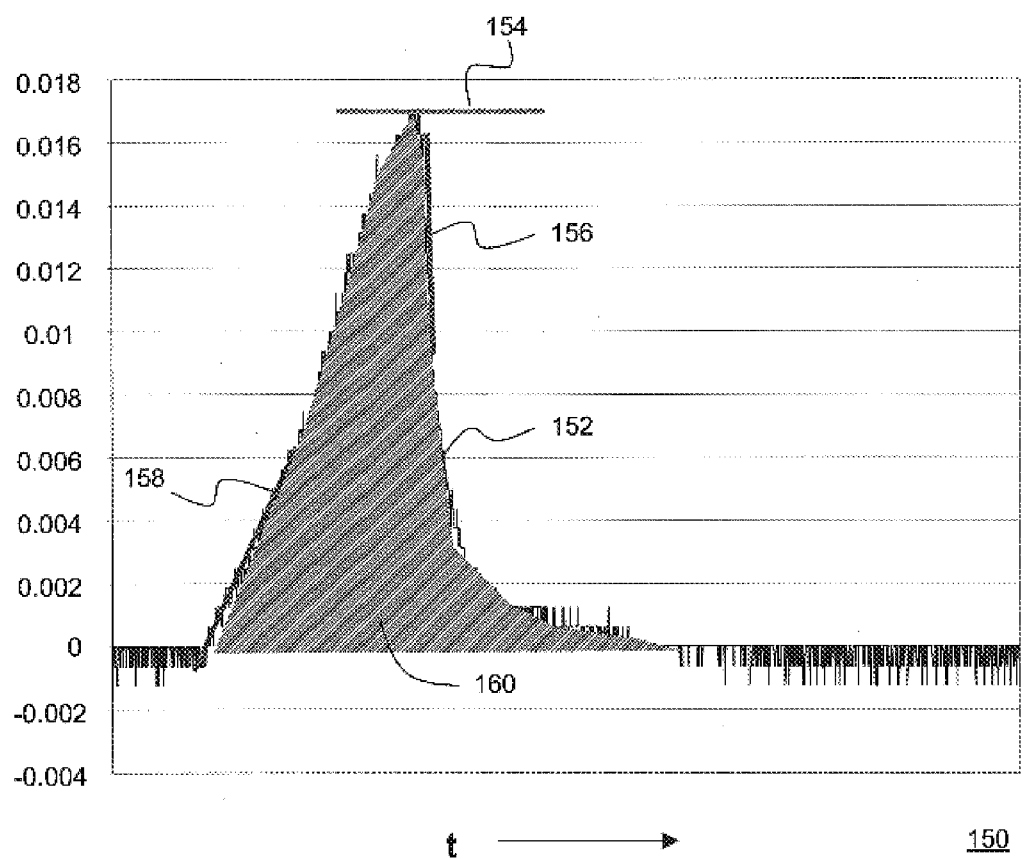
FIG. 2 is a waveform illustrating different attributes (or parameters) that may be derived and/or used in an exemplary embodiment according to the present invention.

FIG. 2 is a graph 150 of a waveform 152 (e.g., profile of weld characteristic captured by one of the detectors) illustrating different attributes (or parameters) that may be measured and/or used in an exemplary embodiment according to the present invention. After the waveform data has been transferred to the data acquisition and processing equipment/ computer, algorithms including simple mathematical, algebraic and/or calculus operations such as maximum, minimum, slopes, integration, etc. may be used to obtain single value outputs for attributes (parameters or properties) that may be useful for distinguishing good welds from bad welds. The algorithms may be normalized to facilitate comparison.

For example, the waveform 152 has properties of a maximum 154, a falling slope 156, a rising slope 158, and an integral 160 of the area under the waveform. In an exemplary embodiment, the algorithms may be implemented using Microsoft® Excel formulas and/or Visual Basic® programming. Microsoft® and Visual Basic® are registered trademarks of Microsoft Corporation, a Delaware corporation, Redmond, Wash.

In an exemplary embodiment according to the present invention, the decision making process is improved by algorithm results having single values for the attributes. Using single values for decision making is typically easier to implement than pattern matching and/or applying advanced mathematical techniques to the acquired waveform. Hence, single data values for the attributes may be used as a quantitative measure of the weld performance. The quantitative result can easily be compared against a predetermined value for a "good" or "bad" judgment. Furthermore, joint quality measurements, themselves single values, may be correlated with algorithm results to provide a measure of joint quality.

Figure 3A:
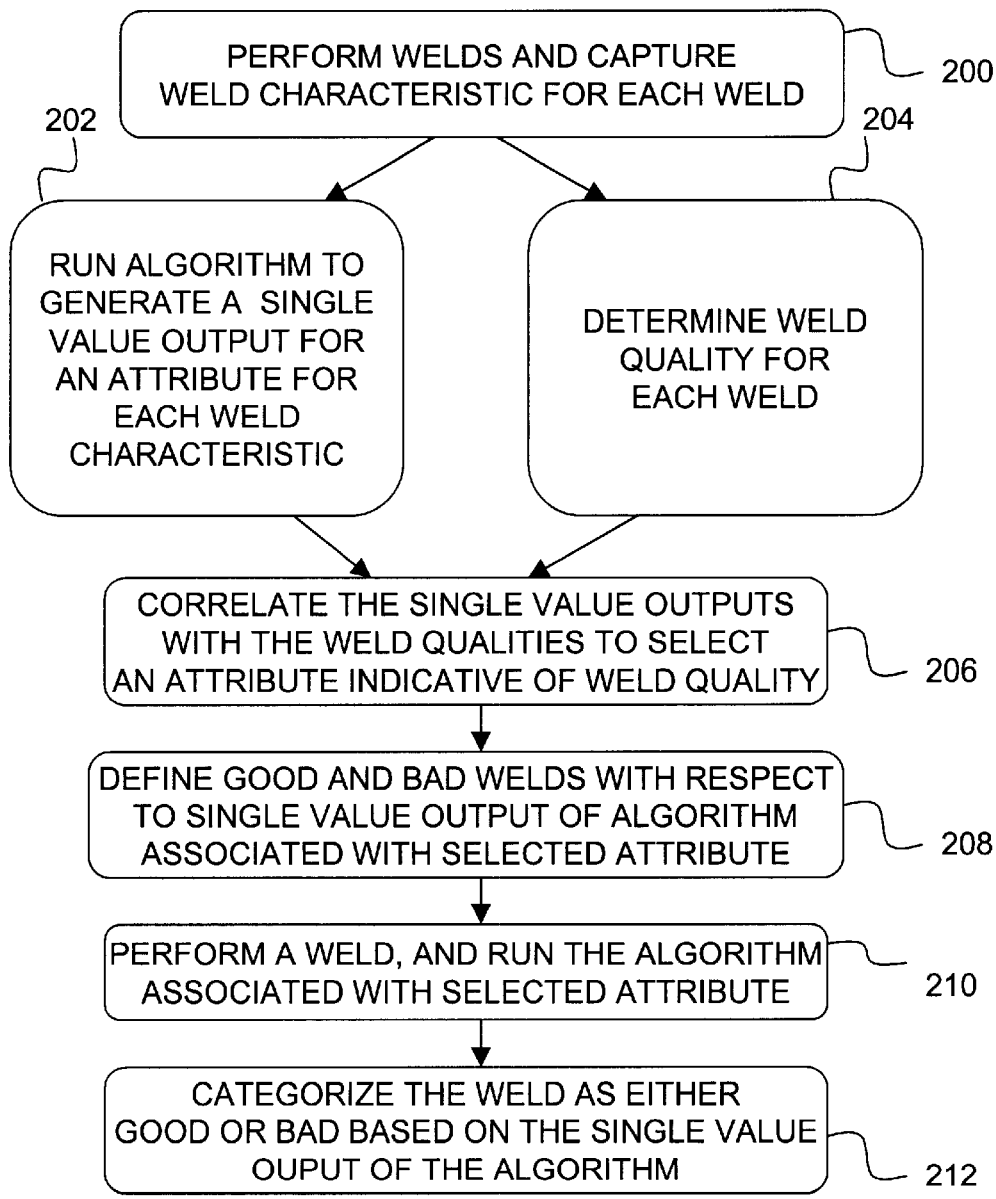
FIG. 3A is a flow diagram illustrating a process development (e.g., for defining good and bad welds based on an attribute of a laser weld characteristic) and process control (e.g., categorizing welds as either good or bad for quality control) in an exemplary embodiment according to the present invention.

FIG. 3A illustrates a process of setting up (i.e., process development) for and performing weld monitoring (i.e., process control) in an exemplary embodiment according to the present invention. Steps 200–208 are process development steps used to initially set up the weld monitor, and are typically run at the beginning of a weld process. On the other hand, steps 210 and 212 are process control steps that may be run repeatedly to provide process control to an on-going weld process.

In step 200, welds (e.g., test welds) are performed and weld characteristics are captured (i.e., profiles of the weld characteristics (e.g., reflection, IR and/or acoustic signal) are taken over time for different laser energy levels, etc.).

Figure 8:
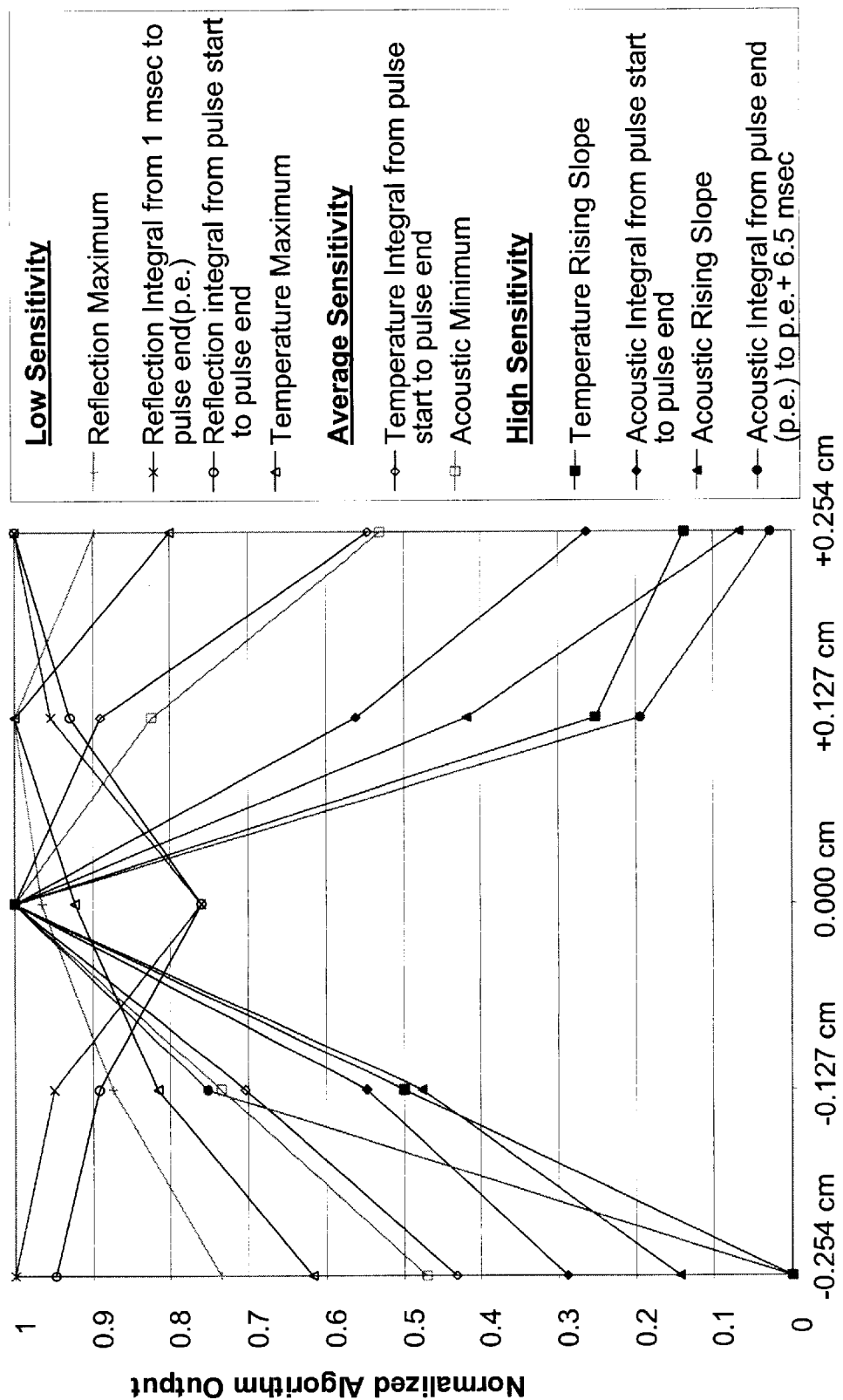
FIG. 8 illustrates graphs for different attributes over focus positions in an exemplary embodiment according to the present invention.

In step 202, single data values are determined for one or more attributes (or parameters) for each weld characteristic by running algorithm(s) selected from a library of algorithms associated with the attributes. For example, for each of the weld characteristics (reflection, acoustic, IR, etc.), the single values for the attributes are determined through mathematical algorithms (maximum, minimum, slopes, integration, other algebraic/calculus functions, etc.) and the single values are plotted. The attributes may also be defined for a time period, for example, starting at the beginning of the laser pulse. All attributes may be represented on the same graph for comparison purposes. For example, FIG. 8 shows a graph of various different attributes with respect to a focus position. It can be seen from FIG. 8 that the values for the attributes change as the focus position varies from in focus to out of focus.

In step 204, a weld quality is determined for each of the welds. Some welds may be determined to be "good" while others may be determined to be "bad." The weld quality may be assessed through physical testing and/or visual inspection. The physical testing may include testing for weld strength, weld interface area, weld cross-section, etc., and may be ascertained through destructive testing. For example in an exemplary embodiment, the weld quality may be determined for five groups of welds, from a) best→ b) good→c) fair→d) poor→ to e) poorest in weld quality. The groups may be defined through different laser settings (e.g., energy level), and each group may contain a number of welds (e.g., 5).

In step 206, the single value outputs of the algorithm(s) (e.g., from step 202) are correlated with the weld qualities (e.g., from step 204) to select an attribute indicative of weld quality. The behavior of the selected attribute should be consistent (e.g., increasing or decreasing function with respect to the optimum case) in order to rely on it for distinguishing good welds from bad welds. For example, in FIG. 8, a number of attributes, such as, for example, temperature (IR) rising slope, acoustic integral, acoustic rising slope, etc., demonstrate high sensitivity as the focus point moves away the focus parameter value of 0.000 cm (exactly in focus).

In step 208, good and bad welds are defined with respect to the single value output of the algorithm associated with the selected attribute for quality control purposes. For example in reference to FIG. 11, any weld with the weld interface area of 0.085 mm$^2$ or more may be deemed to be good, while the weld interface area of less than 0.085 mm$^2$ may be deemed to be bad. As can be seen from FIG. 11, the weld interface area of 0.085 mm$^2$ corresponds roughly with the area under the temperature (IR) curve of approximately 0.007.

In step 210, a weld is performed, and the algorithm associated with the selected attribute is run to obtain a corresponding single value output. Then the weld categorized in step 212 as either good or bad weld based on the single value output of the algorithm. For example, for the weld in step 210, any weld with the temperature (IR) curve of approximately 0.007 (corresponding to the weld interface area of 0.085 mm$^2$) or higher, may be deemed a good weld.

Figure 3B:
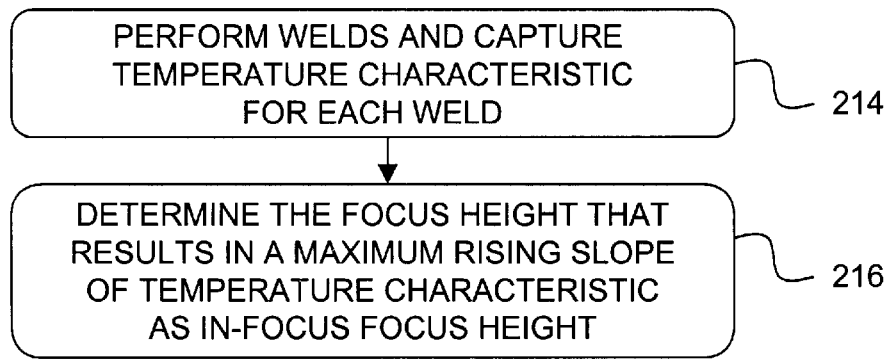
FIG. 3B is a flow diagram illustrating a process of adjusting a focus height of a pulsed laser in an exemplary embodiment according to the present invention.

FIG. 3B is a flow diagram illustrating a process of adjusting a focus height of a pulsed laser in an exemplary embodiment according to the present invention. In step 214, a number of welds (testing welds) are performed, and at least a temperature characteristic is captured for each weld. These welds are performed at a different focus height about a predetermined initial focus height. The initial focus height may be selected by the system developer or by a user, and should roughly be the focus height at which the laser is in-focus.

Thus, for example, the test weld may be performed first at an approximated in-focus focus height, and the focus height may be adjusted up and down about that initial approximated in-focus focus height, while capturing the temperature characteristic at each focus height.

In step 216, a focus height that results in a maximum rising slope (i.e., single value output of the maximum rising slope algorithm or the highest rate of change of temperature) of temperature characteristic is determined as a correct (i.e., in-focus) focus height. This can be considered a special case of the process illustrated in FIG. 3A in that the desired attribute (e.g., maximum rising slope of the temperature characteristic) has already been determined as the attribute indicative of the in-focus focus height. In other embodiments, the attribute indicative of the in-focus focus height may also be selected through running one or more algorithms on the welds, determining weld quality for each weld, and then correlating the single value outputs of the algorithms with the weld qualities.

Figure 4:
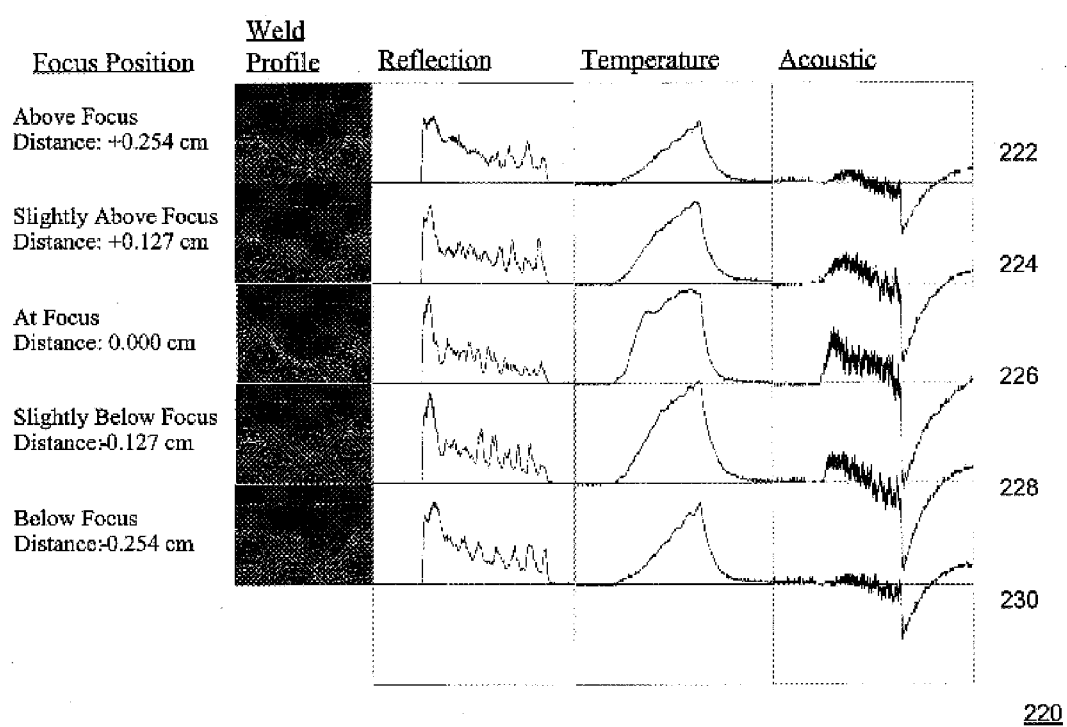
FIG. 4 illustrates waveforms that may be realized for various different laser characteristics depending on the focus position.

FIG. 4 illustrates oscilloscope outputs 220 that represents different profiles based on the focus positions, namely, for focus positions of +0.254 cm, +0.127 cm, 0.000 cm, −0.127 cm and −0.254 cm. The profiles 222 illustrate reflection, IR and acoustic profiles for the above focus distance of +0.254 cm. In addition, the profiles 224 illustrate reflection, IR and acoustics profiles for the above focus distance of +0.127 cm. Further, the profiles 226 illustrate reflection, IR and acoustics profiles for at focus case (i.e., distance of 0.000 cm). The profiles 228 and 230 illustrate profiles for the below focus distance of −0.127 cm and −0.254 cm, respectively.

When taking these profiles, the working distance may be varied during focal position variation welds and the algorithm results may display strong sensitivity to the variation. Spot welds may be performed in a bead-on-plate configuration. A LW50A (a Unitek-Miyachi laser welder) pulsed Nd:YAG laser capable of 5 kW peak power may be used to take the profiles. In other embodiments, any other power-feedback laser may be used to take the profiles.

The laser pulses (e.g., 1 kW, 5J) may produce weld nuggets measuring 0.610 mm in diameter and 0.305 mm in depth while in focus. A z-axis stepper motor may be used for increments of 0.127 cm to change the focus height in an exemplary embodiment according to the present invention.

The trends in the weld profile and raw monitor signals (profiles of the weld characteristics) may be seen in FIG. 4. As can be seen in FIG. 4, the weld profile walls may be steep at focus but may gradually become shallow (conduction weld type) as the focus height moves away from the focal position (above and below focus). Likewise, all of the monitor signals (profiles of the weld characteristics) may change shape when moving from in focus to out of focus.

The temperature (IR) signal may have the largest area under the curve due to a strong up-slope (rising slope) at focus. The temperature (IR) up-slope may decrease and create a triangle shape as the working distance moves out of focus (above and below). At focus, the acoustic signal shape may have maximum values in the beginning and the largest negative dip after the pulse. The positive values and negative dip may become less pronounced away from focus (above and below).

FIGS. 5A–5C, 6A–6C and 7A–7D illustrate processes (mathematical algorithms) for deriving single value outputs for attributes (or parameters) for defining weld quality based on different weld characteristics as the focus point is varied in an exemplary embodiment according to the present invention.

Figure 5A:
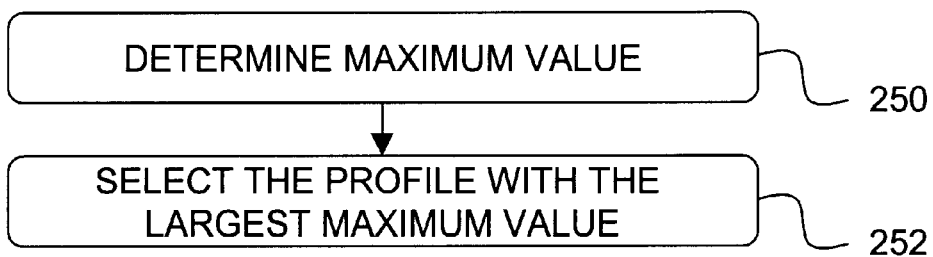
FIGS. 5A–5C illustrate processes for deriving attributes (or parameters) for defining weld quality based on reflection profiles in an exemplary embodiment according to the present invention.
Figure 5B:
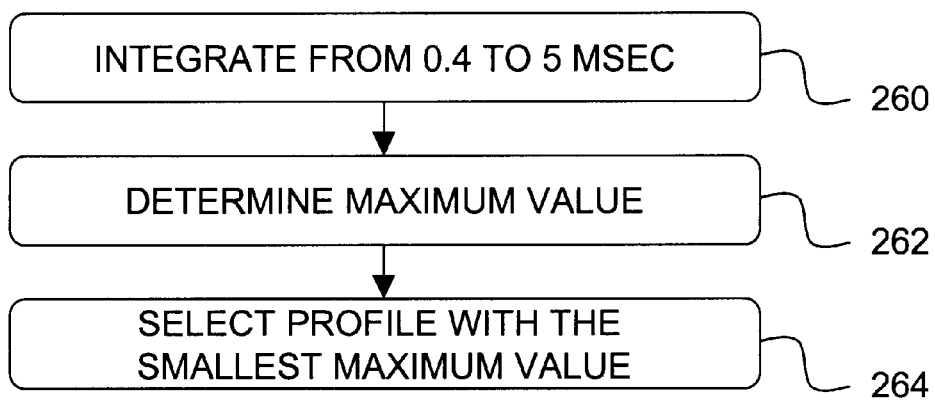
Figure 5C:
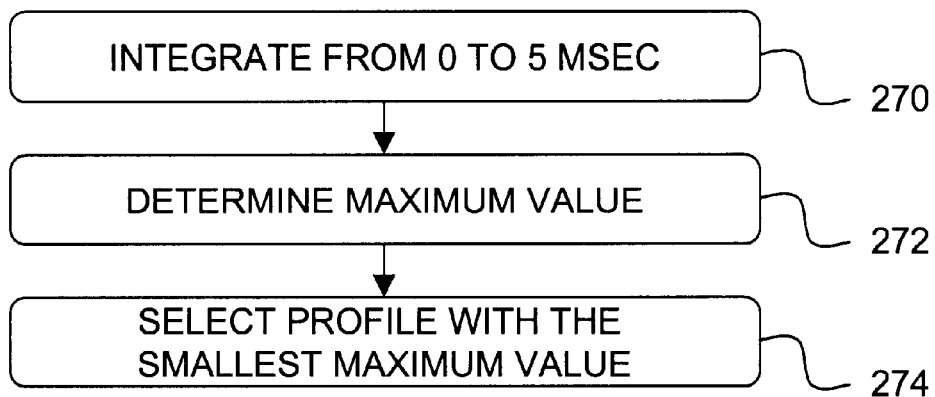

FIGS. 5A–5C illustrate processes (mathematical algorithms) for deriving single value outputs for attributes for defining weld quality based on reflection profiles in an exemplary embodiment according to the present invention. In step 250 of FIG. 5A, the maximum value of the reflection signal is determined for each profile, and the profile with the largest maximum value is selected in step 252 as the profile for the at-focus (or in-focus) weld.

In step 260 of FIG. 5B, the reflection profiles are integrated from 0.4 ms to 5 ms, and the maximum value is determined for each profile in step 262. In step 264, the profile with the smallest maximum value is determined as the profile for the at-focus weld. In step 270 of FIG. 5C, the reflection profiles are integrated from 0 ms to 5 ms, and the maximum value is determined for each profile in step 272. In step 274, the profile with the smallest maximum value is determined as the profile for the at-focus weld.

Figure 6A:
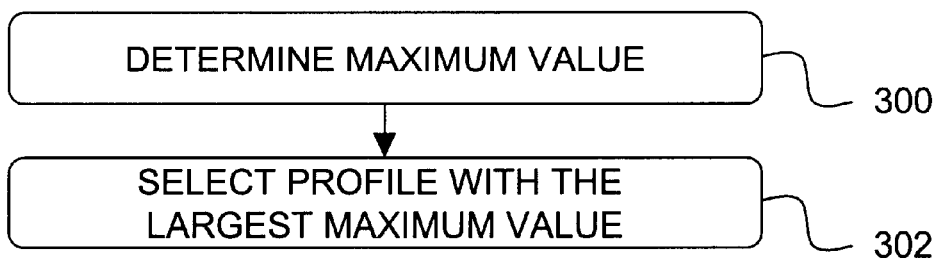
FIGS. 6A–6C illustrate processes for deriving attributes (or parameters) for defining weld quality based on temperature (IR) profiles in an exemplary embodiment according to the present invention.
Figure 6B:
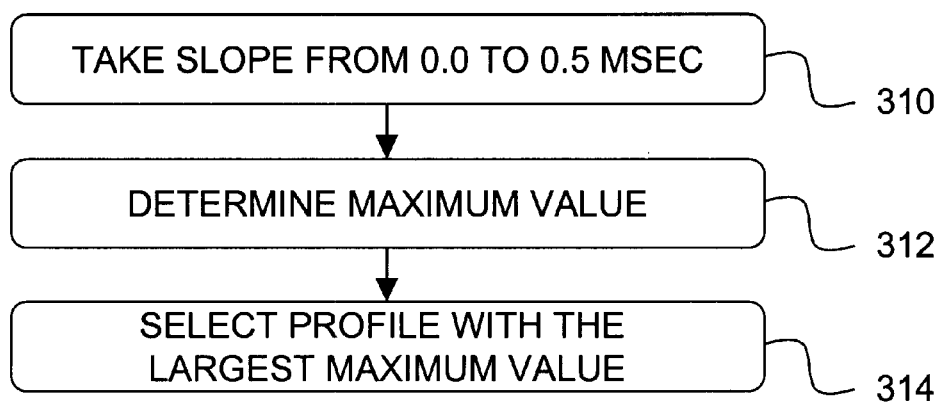
Figure 6C:
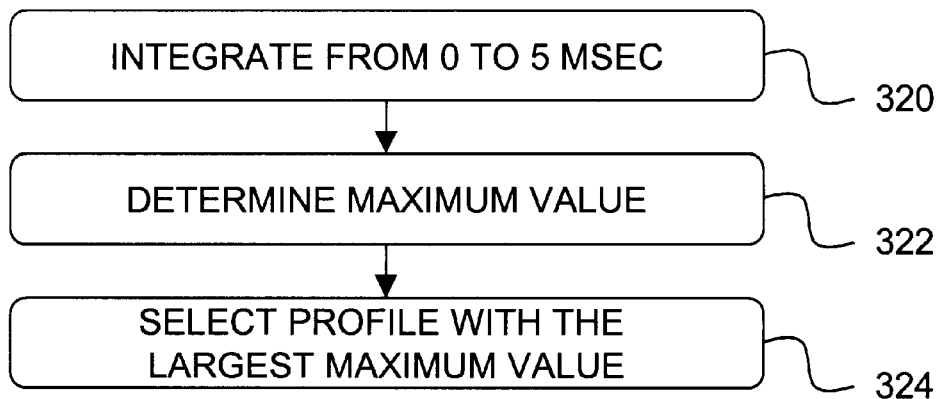

FIGS. 6A–6C illustrate processes (mathematical algorithms) for deriving single value outputs for attributes for defining weld quality based on IR profiles in an exemplary embodiment according to the present invention. In step 300 of FIG. 6A, the maximum value of the reflection signal is determined for each profile, and the profile with the largest maximum value is selected in step 302 as the profile for the at-focus (or in-focus) weld.

In step 310 of FIG. 6B, a slope is taken from 0.0 ms to 0.5 ms, and the maximum value is determined for each profile in step 312. In step 314, the profile with the largest maximum value is determined as the profile for the at-focus weld. In step 320 of FIG. 6C, the IR profiles are integrated from 0 ms to 5 ms, and the maximum value is determined for each profile in step 322. In step 324, the profile with the largest maximum value is determined as the profile for the at-focus weld.

FIGS. 7A–7D illustrate processes (mathematical algorithms) for deriving single value outputs for attributes for defining weld quality based on acoustic profiles in an exemplary embodiment according to the present invention. In step 350 of FIG. 7A, the minimum value of the acoustic signal is determined for each profile, and the profile with the smallest minimum value is selected in step 352 as the profile for the at-focus (or in-focus) weld.

Figure 7A:
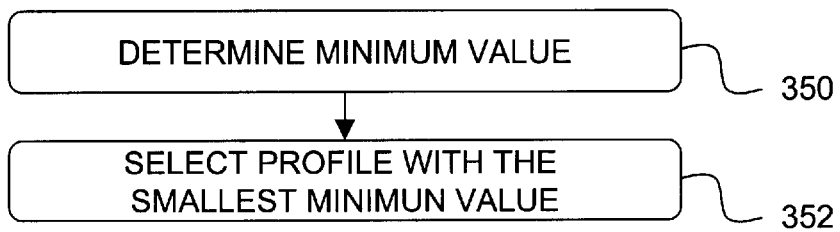
FIGS. 7A–7D illustrate processes for deriving attributes (or parameters) for defining weld quality based on acoustic profiles in an exemplary embodiment according to the present invention.
Figure 7B:
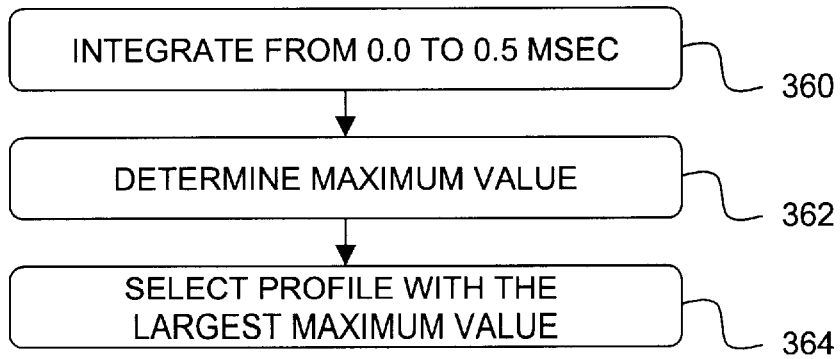
Figure 7C:
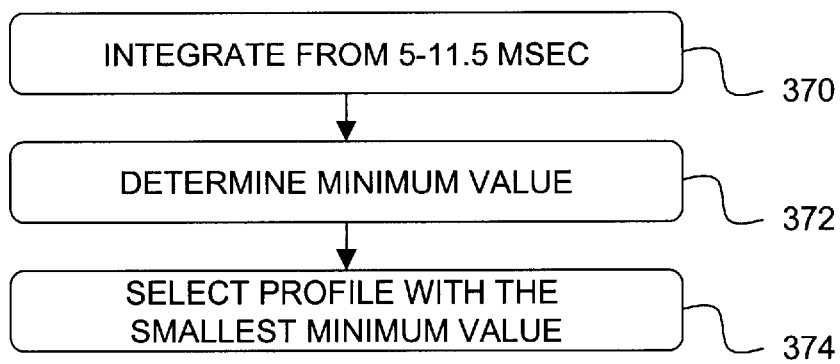
Figure 7D:
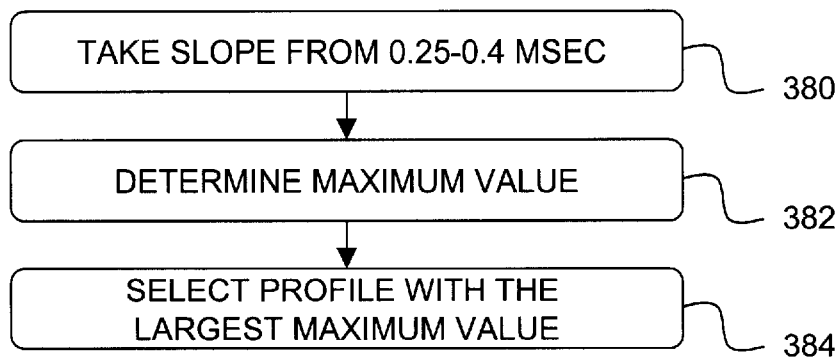

In step 360 of FIG. 7B, the profiles are integrated from 0.0 ms to 0.5 ms, and the maximum value is determined for each profile in step 362. In step 364, the profile with the largest maximum value is determined as the profile for the at-focus weld. In step 370 of FIG. 7C, the acoustic profiles are integrated from 5 ms to 11.5 ms, and the maximum value is determined for each profile in step 372. In step 374, the profile with the smallest minimum value is determined as the profile for the at-focus weld. In step 380 of FIG. 7D, the slope is taken from 0.25 ms to 0.4 ms, and the maximum value is determined for each profile in step 382. In step 384, the profile with the largest maximum value is determined as the profile for the at-focus weld.

It can be seen in FIG. 8 that algorithm results exhibit strong sensitivity to the focal position. The algorithm trends may be categorized as low, average and high sensitivities. High sensitivity algorithms, for example, may have a (normalized) value of 1 at the focal position and low values (<0.3) at the out-of-focus extremes. Lower sensitivity algorithms (e.g., with the maximum of <0.8) may still be useful especially if the measurement variability is low from weld to weld. In the exemplary embodiments as can be seen in the normalized algorithm output 400, IR and acoustic algorithms may be most sensitive to the focal (or focus) position.

Figure 9A:
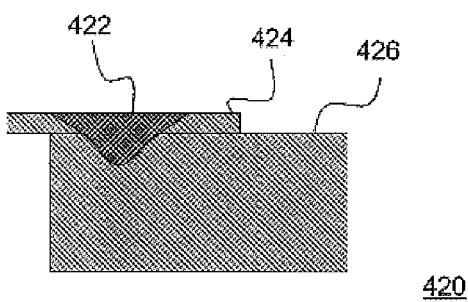
FIGS. 9A–9D illustrate energy levels used for welding and views for a test being performed on two welded surfaces in an exemplary embodiment according to the present invention.

FIG. 9A illustrates a lap joint weld 420, where base materials 424 and 426 are joined together by a weld 422 in an exemplary embodiment according to the present invention. For example, the base material 424 may be a 0.102 mm thick stainless steel (e.g., Type 304) and the base material 426 may be a 0.635 mm thick stainless steel (e.g., Type 304). The laser may be a LW50A laser, and the 400SI optical fiber maybe used to carry laser signal for welding. The laser signal may be focused by 100/100 FX Focus Head (a Unitek-Miyachi FX series focus head) or any other suitable focus head. The welding, for example, may be performed at 4 degree tilt, and approximately 0.480 mm welds may be realized.

The penetration depth may be varied for a lap joint weld. The laser weld monitor results may correlate with the penetration depth variation. The laser pulse energy may be increased by increasing the pulse width at a fixed peak power of 1.4 kW.

Figure 9B:
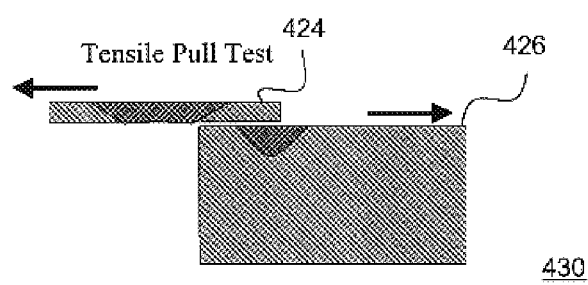
Figure 9C:
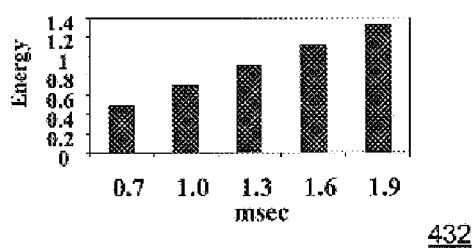
Figure 9D:
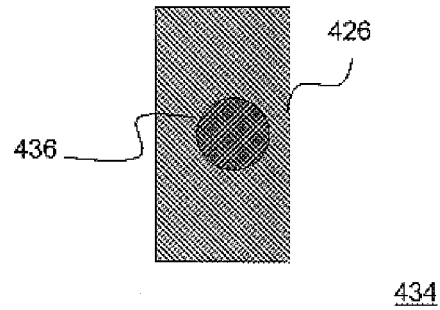

FIG. 9B illustrates performing a tensile pull test 430 to measure the strength of the weld. The tensile pull test is a destructive test where the welded base materials 424 and 426 are pulled apart to measure how much force that they can withstand without breaking apart. FIG. 9C shows different pulse energy applied to effect the welds, and the duration of the pulse, which may vary with the energy levels. FIG. 9D illustrates a top view 434 of a weld interface area 436 on the surface of the bottom base material 426.

Figure 10:
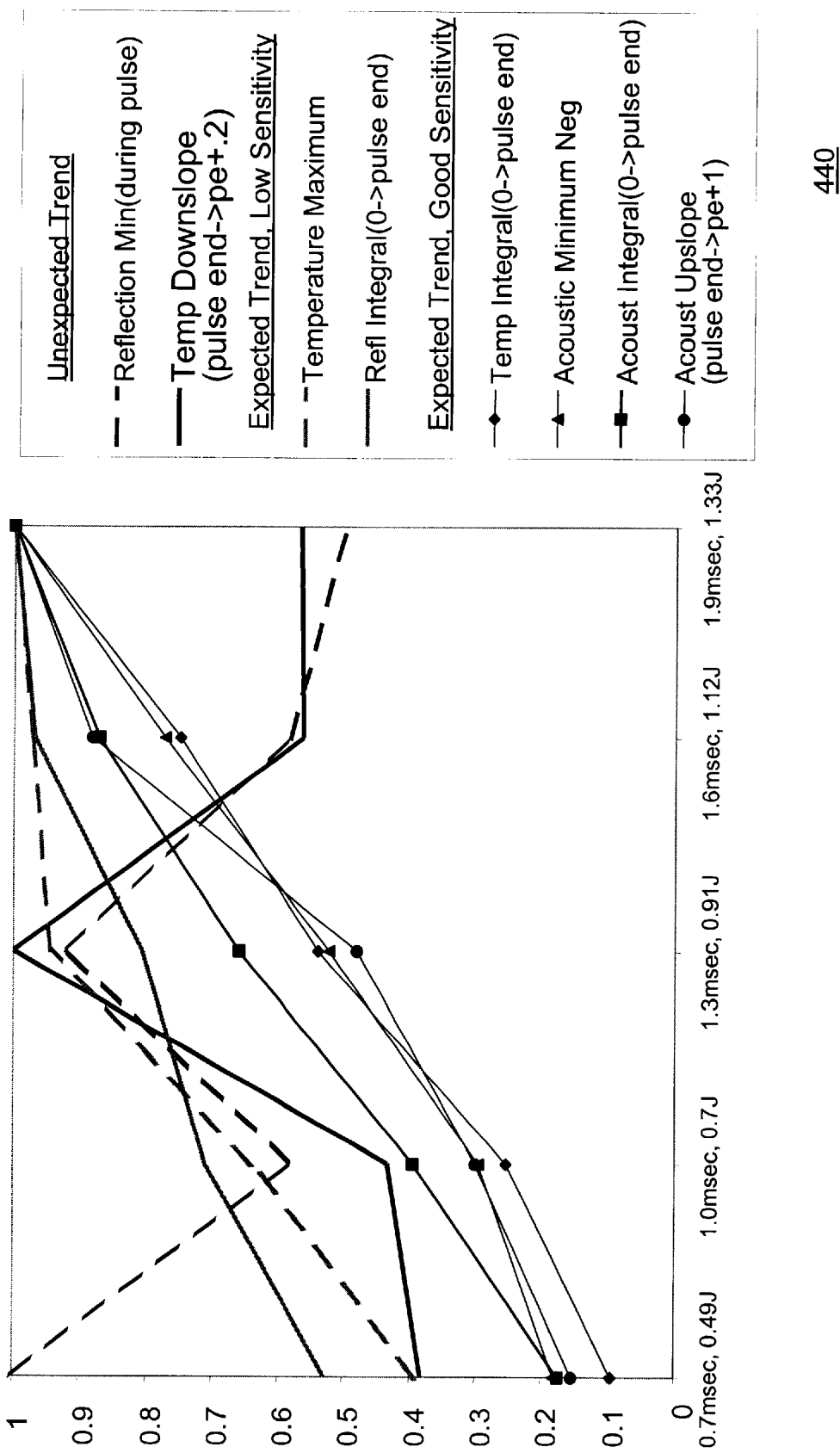
FIG. 10 illustrates graphs of attributes (or parameters) generated using different algorithms used during welding in an exemplary embodiment according to the present invention.

In exemplary embodiments of the present invention, a number of algorithms are developed and applied to the raw monitor signals (profiles for the weld characteristics). FIG. 10 illustrates graphs 440 of single value outputs for attributes generated from different algorithms applied to weld characteristics for different weld penetration depths in an exemplary embodiment according to the present invention. It can be seen that some trends are unexpected, some are expected but have low sensitivity, while some are expected and have good sensitivity. The expected trends having good sensitivity, for example, are temperature (IR) integral, acoustic minimum negative, acoustic integral and acoustic upslope, as can be seen on FIG. 10.

The lap welds may be repeated with multiple welds at each setting. FIGS. 11–14 illustrate the results of the correlation between weld strength and monitor signals in an exemplary embodiment according to the present invention. The linear fit between the acoustic integral and quality outputs (interface area and tensile strength), for example, may maintain an $R^2$ value greater than 0.95 and the temperature (IR) integral fit may reach similar $R^2$ values.

Multiple welds may be performed for repeatability measurement purposes. The scatter of data points may be indicative of both the monitor and joint quality measurement variation. The strong correlation may be maintained over multiple welds, and would indicate the potential of the exemplary embodiment or use in industrial applications.

Figure 11:
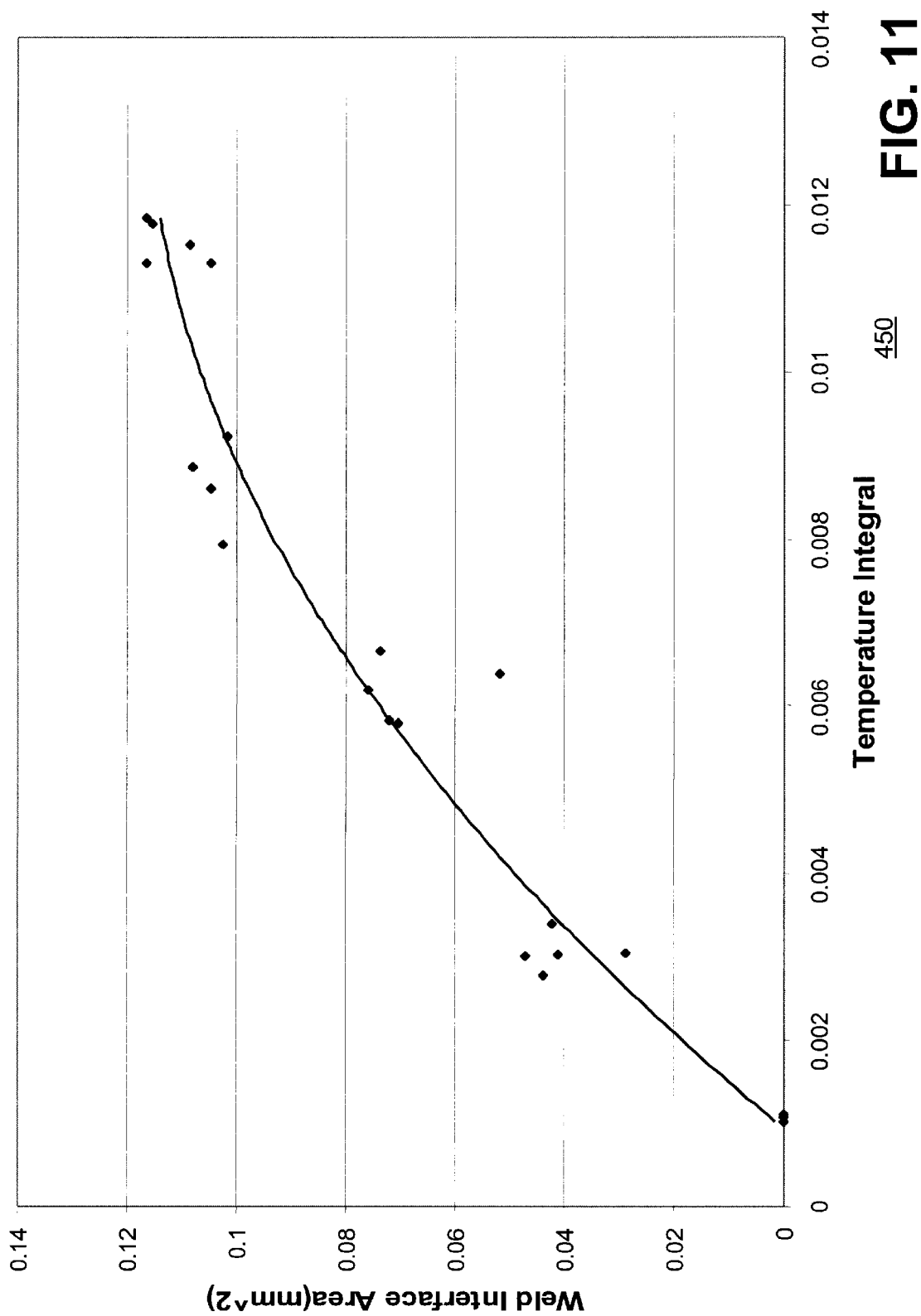
FIG. 11 illustrates a correlation between temperature (IR) integral and weld interface area in an exemplary embodiment according to the present invention.
Figure 12:
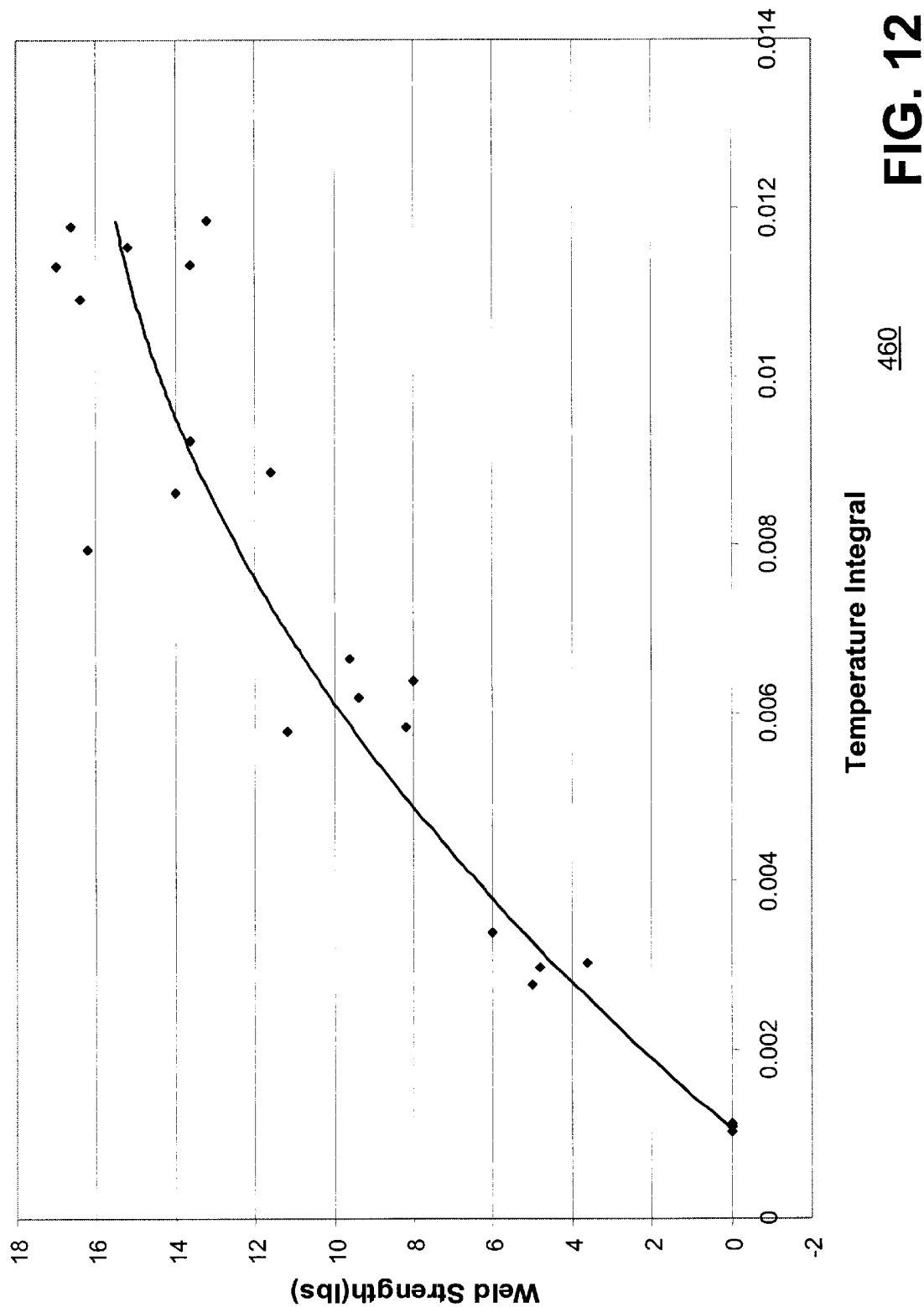
FIG. 12 illustrates a correlation between temperature (IR) integral and weld strength in an exemplary embodiment according to the present invention.
Figure 13:
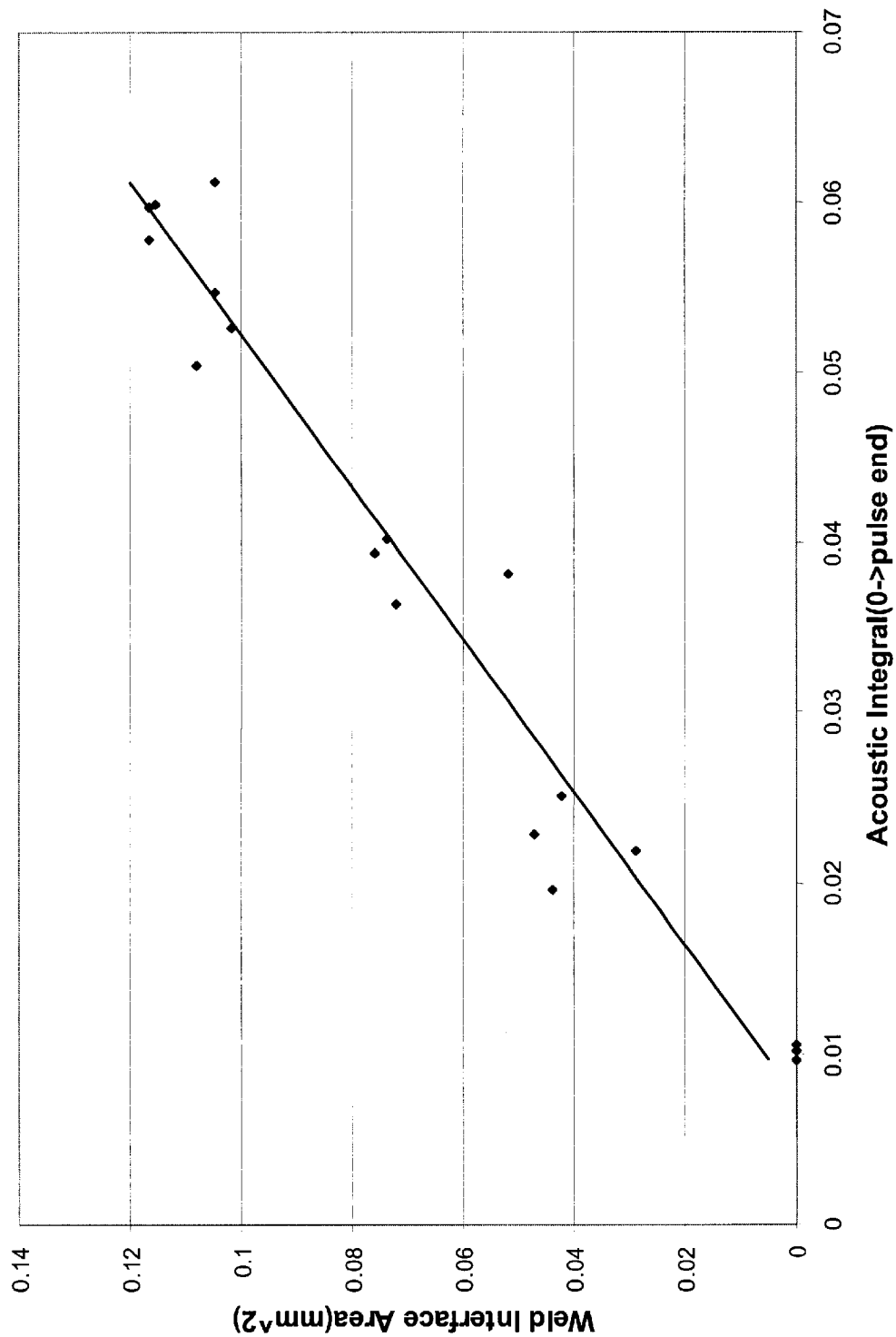
FIG. 13 illustrates a correlation between acoustic integral and weld interface area in an exemplary embodiment according to the present invention.
Figure 14:
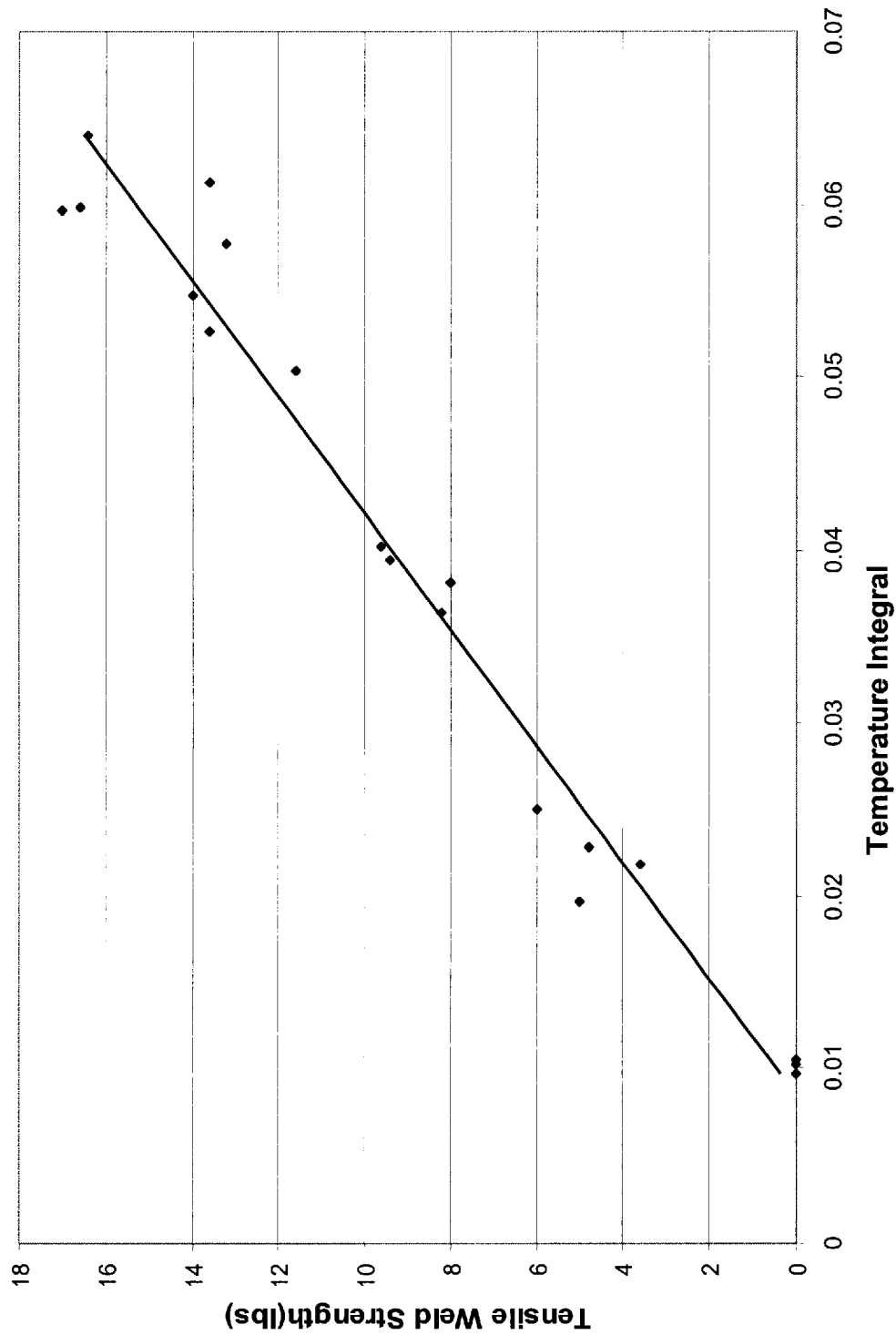
FIG. 14 illustrates a correlation between temperature (IR) integral and weld strength in an exemplary embodiment according to the present invention.

FIG. 11 illustrates a graph 450 of a correlation between weld interface area and temperature (IR) integral. The data points are fitted with a curve $y=-712.31x^2+19.558x-0.0178$ and $R^2=0.9643$. FIG. 12 illustrates a graph 452 of a correlation between weld strengths (lbs) and temperature (IR) integral. The data points are fitted with a curve $y=-93681x^2+2641.6x-2.6676$ and $R^2=0.9434$. FIG. 13 illustrates a graph 470 of a correlation between weld interface area and acoustic integral. The data points are fitted with a curve $y=-2.2322x -0.0167$ and $R^2=0.9598$. FIG. 14 illustrates a graph 480 of a correlation between tensile weld strength and temperature (IR) integral. The data points are fitted with a curve $y=-296.72x -2.5192$ and $R^2=0.972$.

Figure 15:
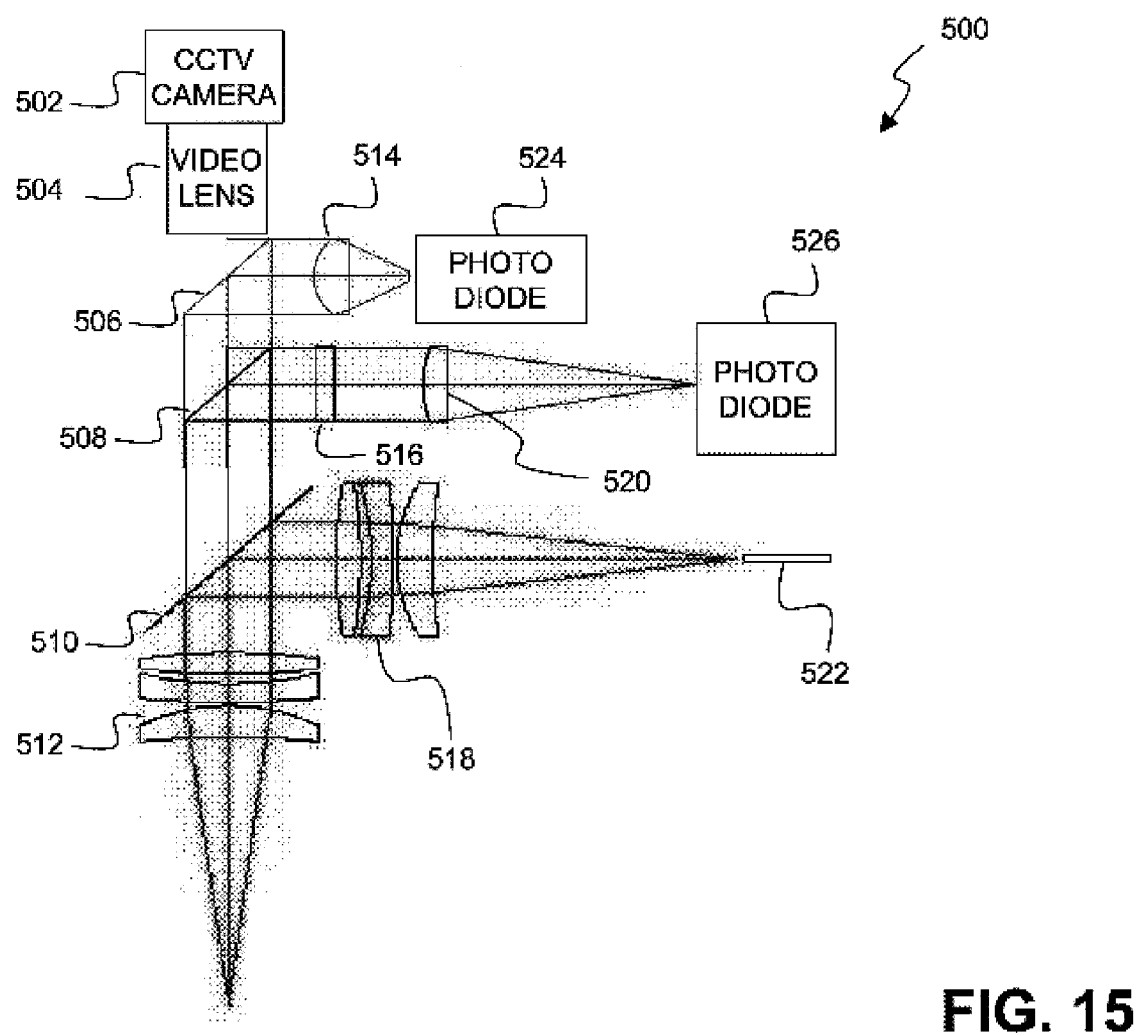
FIG. 15 is a block diagram of a laser weld monitoring system for capturing weld characteristics in another exemplary embodiment according to the present invention.

FIG. 15 is a block diagram of a weld monitoring system 500 for capturing (or measuring) and analyzing laser weld characteristics in another exemplary embodiment according to the present invention. In this embodiment, reflected laser radiation (i.e., reflection signal) and infrared radiation (i.e., IR signal) are captured by photodiodes 526 and 524, respectively. Further, a closed circuit television (CCTV) camera 502 is used to capture images of welding parts prior to and/or after welding. Many of the components in the system 500 of FIG. 15 may be similar or identical to the components in the system 100 of FIG. 1. Further, the output of the photodiodes and/or the CCTV camera may be provided for processing and analysis to a digitizer and/or a data acquisition and processing equipment similar to the one used in the system 100.

The photodiode 526 is used to measure the reflection signal (e.g., 1064 nm) from the weld surface. The photodiode 526, for example, may be a Si (silicon) photodiode with a peak response at 800 nm. Further, the photodiode 524 is used to measure the IR signal. The photodiode 524, for example, may be an InGaAs (indium gallium arsenide) photodiode with a peak response at 1550 nm. In other embodiments, other sensors or detectors (e.g., monitor sensor, machine vision sensor, etc.) instead of or in addition to the photodiodes 524 and/or 526 may be used to measure laser weld characteristics.

A laser signal may be provided via a fiber optic cable 522, which may be any suitable optical fiber. The laser signal may be provided by a pulsed 1064 nm Nd:YAG laser. At the output of the fiber optic cable 522, the laser signal passes through a collimator 518, which may be any suitable collimator. The laser signal then may be applied to a dichroic mirror 510, which for example, may reflect 99.5% at 1064 nm and 10% at 633 nm. The reflected laser signal is focused by a suitable focus lens 512 onto a weld surface.

Some portion of the laser signal is reflected back from the weld surface. The reflected signal passes back through the focus lens 512 and the dichroic mirror 510, reflects off the dichroic mirror 508 (e.g., 100% at 1064 nm and 10% at 663 nm), gets filtered at 1064 nm with an interference filter 516 (e.g., 1064+/−10 nm interference filter), and is focused onto the photodiode 526 by a lens 520, which for example, may be a 75 mm (mili-meter) plano-convex lens.

An IR signal from the weld surface passes through the focus lens 512 and the dichroic mirrors, and is applied to a semiconductor laser mirror 506, which for example, may reflect 100% at 1400–1700 nm. For high temperature processes, the semiconductor laser mirror 506 may be substituted with a 1200–1300 nm mirror. The IR signal is then focused on to the photodiode 524 by a lens 514, which for example, may be a 25 mm plano-convex lens. In this embodiment, long pass filters, such as the long pass filters 106 of FIG. 1, may not be needed, because the semiconductor laser mirror 506 reflects radiation between the wavelength of 1400–1700 nm to the photodiode 524.

The portion of the optical signal from laser weld not reflected by the dichroic mirrors or the semiconductor laser mirror 506 is provided to the CCTV camera 502 through a video lens 504. In the described embodiment, the CCTV camera 502 is co-axial with the weld process. In other words, the camera is aligned to the position where the weld will take place. As compared to the laser welding system 100 of FIG. 1, the working distance of camera may be increased, and may result in a comparatively reduced field of view and/or magnification.

Figure 16A:
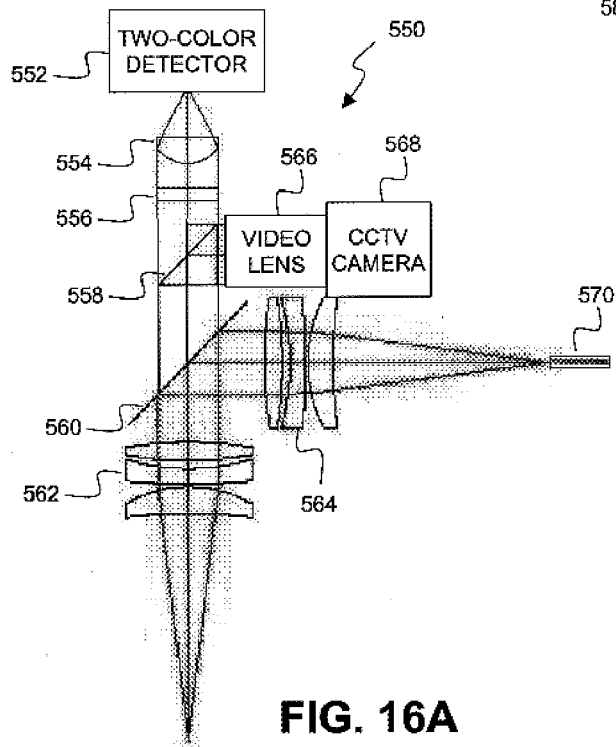
FIG. 16A is a block diagram of a laser weld monitoring system for capturing weld characteristics in yet another exemplary embodiment according to the present invention.

FIG. 16A is a block diagram of a weld monitoring system 550 for capturing (or measuring) and analyzing laser weld characteristics in yet another exemplary embodiment according to the present invention. In this embodiment, reflected laser radiation (i.e., reflection signal) and infrared radiation (i.e., IR signal) are captured by a two-color detector 552. Further, a closed circuit television (CCTV) camera 568 is used to capture images of welding parts prior to and/or after welding. In other embodiments, other sensors or detectors (e.g., monitor sensor, machine vision sensor, etc.), instead of or in addition to the two-color detector 552, may be used to measure laser weld characteristics.

Many of the components in the system 550 of FIG. 16A may be similar or identical to the components in the system 100 of FIG. 1. Further, the output of the photodiodes and/or the CCTV camera may be provided for processing and analysis to a digitizer and/or a data acquisition and processing equipment similar to the one used in the system 100.

A laser signal may be provided via a fiber optic cable 570, which may be any suitable optical fiber. The laser signal may be provided by a 1064 nm pulsed Nd:YAG laser. At the output of the fiber optic cable 570, the laser signal passes through a collimator 564, which may be any suitable collimator. The laser signal then may be applied to a dichroic mirror 560, which for example, may reflect 99.5% at 1064 nm and 10% at 633 nm. The reflected laser signal is focused by a suitable focus lens 562 onto a weld surface.

The optical signal from the weld process includes the reflection signal and the IR signal as well as other optical signals. The optical signal passes through the focus lens 562 and the dichroic mirror 560, and applied to a cold mirror 558. The cold mirror 558, for example, may reflect 90% at 450–750 nm and may reflect only 10% in IR (infrared). The portion of the optical signal reflected by the cold mirror 558 is provided to the CCTV camera 568 through a video lens 566.

The portion of the optical signal that passes through the cold mirror 558 is applied to the two-color detector 552 through a lens 554, which for example, may be a 25 mm piano convex lens. The optical signal portion may also be passed through a 1.2–1.31 μm semiconductor mirror or a longpass filter (>1μm), either of which is optional.

Figure 16B:
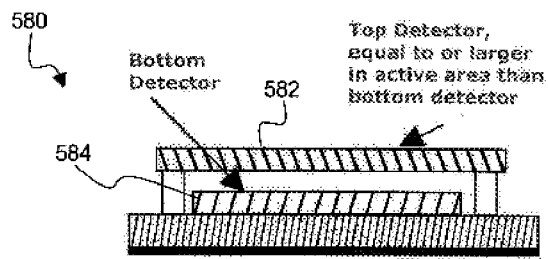
FIG. 16B is a cross-sectional diagram of a two-color detector, which may be applied to the laser weld monitoring system of FIG. 16A.

FIG. 16B is a cross-sectional diagram of a two-color detector 580, which may be applied as the two-color detector 552 of FIG. 16A. The two-color detector 580 includes a top detector 582 and a bottom detector 584. As can be seen from FIG. 16B, the top detector 582 has an active area greater than equal to that of the bottom detector 584. The top detector, for example, may be a silicon detector for detecting the reflection signal at 1064 nm. The bottom detector, for example, may be an InGaAs detector for detecting the IR signal at 1200–1700 nm.

Figure 16C:
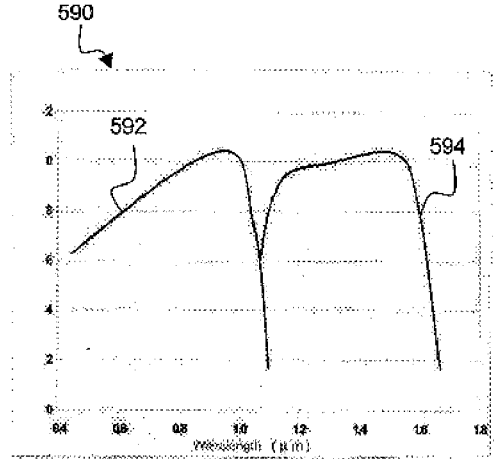
FIG. 16C illustrates detector responses for the detectors that make up the two-color detector of FIG. 16B.

FIG. 16C illustrates detector responses 592 and 594 for the detectors that make up the two-color detector of FIG. 16B. The detector response 592, for example, is for the top detector (e.g., silicon detector) with the peak around 1000 nm, and the detector response 594, for example, is for the bottom detector (e.g., InGaAs detector) with the peak around 1500 nm.

As compared to the system 100 of FIG. 1, the system 550 is more compact in size, and includes fewer components. Further, working or image distance of the CCTV camera 568 is not lengthened appreciably. However, when a two-color detector is used, IR radiation may be reduced by 30% as it passes through the top detector (i.e., Si detector). Further, the top detector may not absorb all of the 1064 nm signal, and may contaminate the signal applied at the InGaAs detector.

Figure 17:
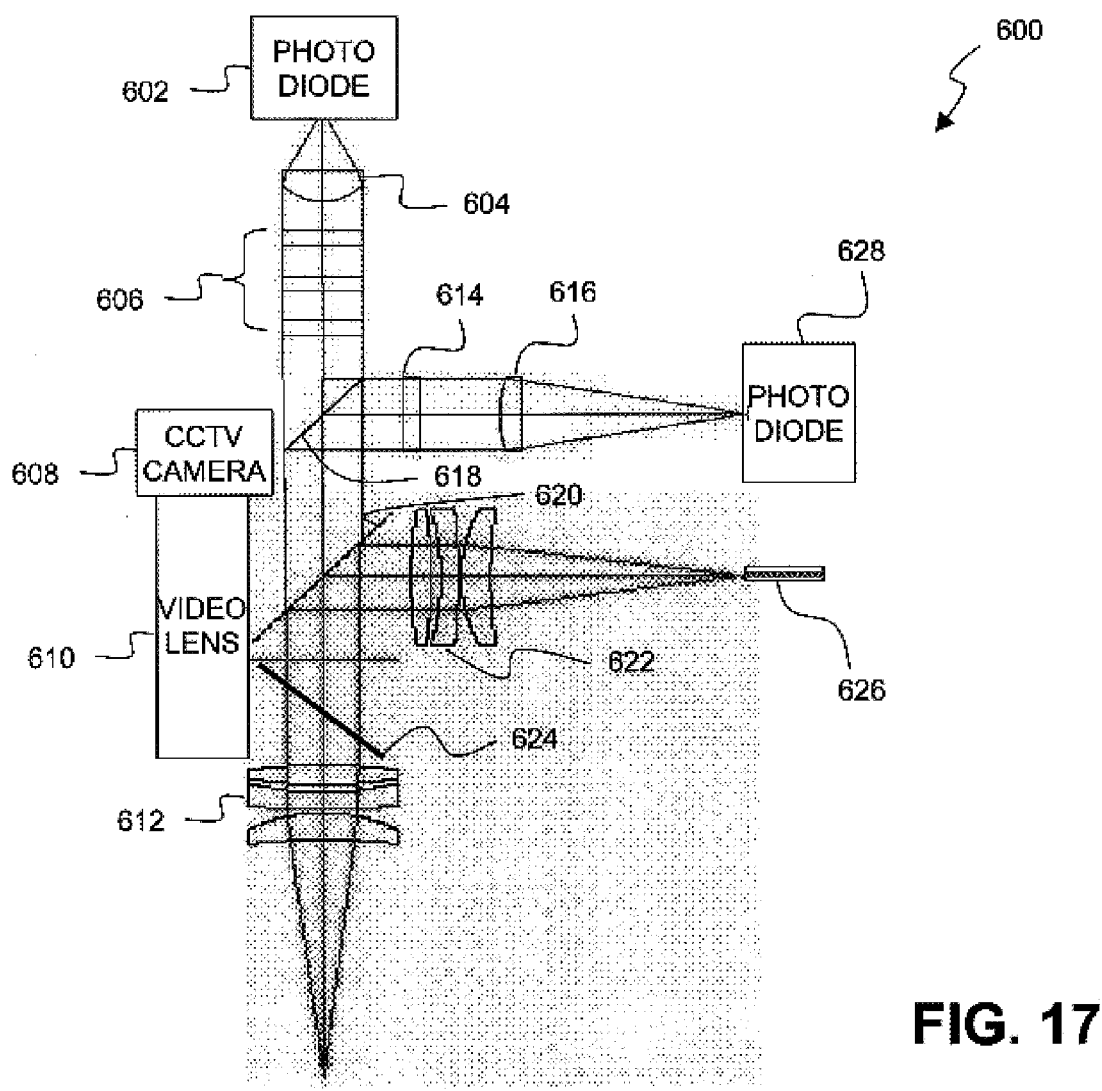
FIG. 17 is a block diagram of a laser weld monitoring system for capturing weld characteristics in still another exemplary embodiment according to the present invention.

FIG. 17 is a block diagram of a weld monitoring system 600 for capturing (or measuring) and analyzing laser weld characteristics in still another exemplary embodiment according to the present invention. In this embodiment, reflected laser radiation and infrared radiation are captured by photodiodes 602 and 628, respectively. Further, a closed circuit television (CCTV) camera 608 is used to capture images of welding parts prior to and/or after welding. Many of the components in the system 600 of FIG. 17 may be similar or identical to the components in the system 100 of FIG. 1. Further, the output of the photodiodes and/or the CCTV camera may be provided for processing and analysis to a digitizer and/or a data acquisition and processing equipment similar to the one used in the system 100.

The photodiode 628 is used to the reflection signal (e.g., 1064 nm) from the weld surface. The photodiode 628, for example, may be a Si (silicon) photodiode with a peak response at 800 nm. Further, the photodiode 602 is used to measure the IR signal. The photodiode 602, for example, may be an InGaAs photodiode with a peak response at 1550 nm. In other embodiments, other sensors or detectors (e.g., monitor sensor, machine vision sensor, etc.) instead of or in addition to the photodiodes 602 and/or 628 may be used to measure laser weld characteristics.

A laser signal may be provided via a fiber optic cable 626, which may be any suitable optical fiber. The laser signal may be provided by a pulsed 1064 nm Nd:YAG laser. At the output of the fiber optic cable 626, the laser signal passes through a collimator 622, which may be any suitable collimator. The laser signal then may be applied to a dichroic mirror 620, which for example, may reflect 9.5% at 1064 nm and 10% at 633 nm. The reflected laser signal then passes through a cold mirror 624 and is focused by a suitable focus lens 612 onto a weld surface. The cold mirror 624, for example, may reflect 90% at 450–750 mm and 10% at IR.

An optical signal from the weld surface is applied first at the cold mirror 624 through the focus lens 612. The 450–750 nm component of the optical signal is mostly reflected by the cold mirror 624 for detection by the CCTV camera 608 through a video lens 610. In this embodiment, the CCTV camera 608 is coaxial with the weld process, and working or image distance of the camera is shortened. The cold mirror 612 may reflect and absorb some of the IR radiation.

The reflection signal passes back through the dichroic mirror 620, reflects off the dichroic mirror 618 (e.g., 100% at 1064 nm and 10% at 663 nm), gets filtered at 1064 nm with an interference filter 614 (e.g., 1064+/−10 nm interference filter), and is focused onto the photodiode 628 by a lens 616, which for example, may be a 75 mm (mili-meter) plano-convex lens.

The IR signal from the weld surface passes through the focus lens 612, the cold mirror 624 and the dichroic mirrors, and gets filtered by three long pass filters 106 (e.g., at >1400 nm), and is focused on to the photodiode 602 by a lens 604, which for example, may be a 25 mm plano-convex lens.

Figure 18:
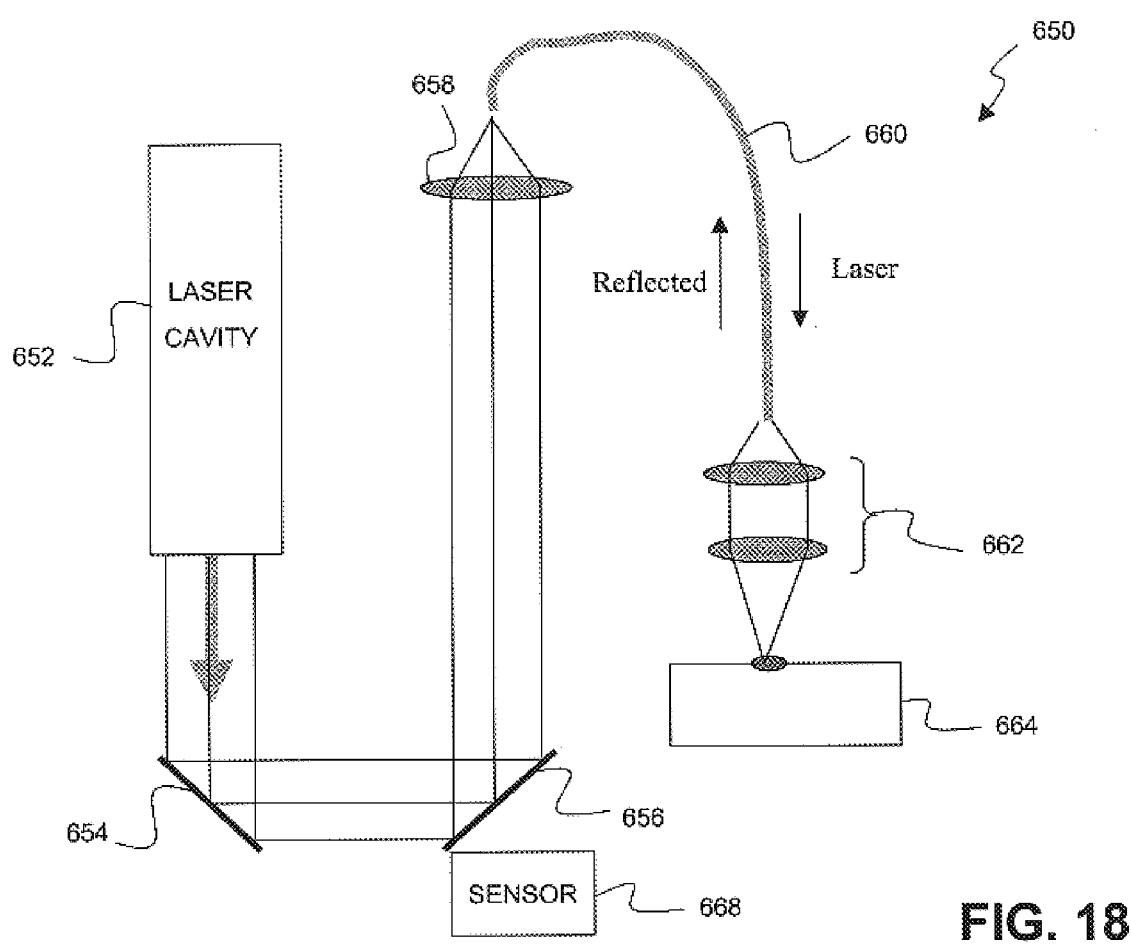
FIG. 18 is a block diagram of a laser weld monitoring system having an internal sensor in an exemplary embodiment according to the present invention.

In an exemplary embodiment according to the present invention, a sensor 668 (e.g., weld monitor sensor) is internal to the laser as illustrated in a laser system 650 of FIG. 18. The laser system includes a laser cavity 652, which provides a laser output. The laser output is reflected by mirrors 654 and 656, and then coupled to a multi-mode optical fiber 660 via a fiber input coupler 658. The laser output is applied at the end of the multi-mode optical fiber 660 to an end effector 662, and then to a weld surface 664. A reflected laser signal is provided back to the laser, and is detected by the sensor 668. Using an internal sensor, such as the sensor 668, may result in an improved space allotment near the weld.

Although this invention has been described in certain specific exemplary embodiments, many additional modifications and variations would be apparent to those skilled in the art. It is therefore to be understood that this invention may be practiced otherwise than as specifically described. Thus, the present embodiments of the invention should be considered in all respects as illustrative and not restrictive, the scope of the invention to be determined by the appended claims and their equivalents.

For example, in other embodiments, different welds may be performed to assess weld characteristics, and generate profiles therefrom. For example, in other embodiments, interface gap variations, butt weld joint variations and/or fillet joint weld variations may be performed to obtain weld characteristics and develop algorithms for weld quality control.

We claim:

1. A laser weld monitoring system capable of assessing a weld quality of welding using a pulsed laser, said system comprising:

at least one sensor capable of capturing a weld characteristic of welding using said pulsed laser, said weld characteristic having a plurality of attributes; and data acquisition and processing equipment adapted for storing and analyzing said weld characteristic, wherein a user performs a plurality of welds to capture at least one weld characteristic for each weld, determines the weld quality of each weld, runs at least one of a library of algorithms associated with the attributes on said at least one weld characteristic for each weld to generate a single value output for the associated attribute, and selects an attribute indicative of the weld quality by correlating the single value outputs of said at least one algorithm with the weld qualities of the welds.

2. The laser weld monitoring system according to claim 1, wherein the user performs the welds at different weld conditions to correlate a variation in the weld quality with the variation in the single value output for said at least one algorithm as the weld conditions change.

3. The laser weld monitoring system according to claim 1, wherein the user determines the weld quality of each weld by performing a physical testing.

4. The laser weld monitoring system according to claim 1, wherein the user determines the weld quality of each weld by performing a visual inspection.

5. The laser weld monitoring system according to claim 1, wherein said at least one sensor includes at least one selected from a group consisting of a photodiode, a microphone, a monitor sensor, a plasma sensor and a machine vision sensor.

6. The laser weld monitoring system according to claim 1, wherein said weld characteristic includes at least one selected from a group consisting of a reflection signal, an IR signal and an acoustic signal.

7. The laser weld monitoring system according to claim 1, wherein said attributes include at least one selected from a group consisting of a maximum, a minimum, a slope, an integration, at least one algebraic function and at least one calculus function.

8. The laser weld monitoring system according to claim 1, wherein said pulsed laser is selected from a group consisting of a feedback laser, a non-feedback laser, an Nd:YAG laser, a $CO_2$ laser and a green laser.

9. The laser weld monitoring system according to claim 1, further comprising a CCTV camera capable of capturing images of welding parts.

10. The laser weld monitoring system according to claim 1, wherein the data acquisition and processing equipment comprises a digitizer for processing said weld characteristic, wherein said digitizer comprises at least one selected from a group consisting of an oscilloscope, a digital oscilloscope, a DSP board, a DAQ board and custom electronics.

11. The laser weld monitoring system according to claim 1, wherein the library of algorithms associated with the attributes have been predetermined by a developer of said laser weld monitoring system.

12. The laser weld monitoring system according to claim 1, wherein the library of algorithms associated with the attributes are developed by the user.

13. The laser weld monitoring system according to claim 1, wherein the system can be used for both process development and process control.

14. A method of monitoring a weld quality of a pulsed laser, said method comprising:

performing a plurality of test welds;

capturing at least one weld characteristic of each test weld, said at least one weld characteristic having a plurality of attributes;

determining the weld quality of each test weld;

running at least one of a library of algorithms associated with the attributes on said at least one weld characteristic for each weld to generate a single value output for the associated attribute; and selecting an attribute indicative of the weld quality by correlating the single value outputs of said at least one algorithm with the weld qualities of the test welds.

15. The method according to claim 14, wherein performing the plurality of test welds comprises performing the testing welds at different weld conditions to correlate a variation in the weld quality with the variation in the single value output for said at least one algorithm as the weld conditions change.

16. The method according to claim 14, wherein running at least one of a library of algorithms comprises generating the single value output for at least one attribute selected from a group consisting of a maximum, a minimum, a slope, an integration, at least one algebraic function and at least one calculus function.

17. The method according to claim 14, wherein determining the weld quality comprises performing a weld strength test.

18. The method according to claim 14, wherein determining the weld quality comprises performing a weld interface area test.

19. The method according to claim 14, further comprising defining good and bad welds based on the single value output of the algorithm associated with the selected attribute.

20. The method according to claim 19, further comprising:

performing a weld;

capturing the weld characteristic of the weld; and running the algorithm associated with the selected attribute on the weld characteristic for the weld to generate the single value output.

21. The method according to claim 20, further comprising determining the weld to be either a good weld or a bad weld by comparing the single value output for the weld with the definition of good and bad welds.

22. A method of adjusting a focus height of a pulsed laser, said method comprising:

performing a plurality of test welds, each test weld being performed at a different focus height about a predetermined initial focus height;

capturing a temperature characteristic of each test weld; and determining the focus height that results in a maximum rising slope in the temperature characteristic as a correct focus height.

* * * * *